(12) United States Patent
Niida et al.

(10) Patent No.: US 6,733,441 B2
(45) Date of Patent: May 11, 2004

(54) ENDOSCOPE DEVICE

(75) Inventors: Koichi Niida, Hachioji (JP); Manabu Yajima, Hino (JP); Tomoki Iwasaki, Hachioji (JP)

(73) Assignee: Olympus Corporation, Tokyo (JP)

( * ) Notice: Subject to any disclaimer, the term of this patent is extended or adjusted under 35 U.S.C. 154(b) by 27 days.

(21) Appl. No.: 09/852,412

(22) Filed: May 10, 2001

(65) Prior Publication Data
US 2002/0045801 A1 Apr. 18, 2002

(30) Foreign Application Priority Data

May 11, 2000 (JP) .................................... 2000-138984
Dec. 19, 2000 (JP) .................................... 2000-385620

(51) Int. Cl.$^7$ ............................................... A61B 1/06
(52) U.S. Cl. ..................................... 600/178; 600/118
(58) Field of Search ................................ 600/160, 178, 600/180, 181

(56) References Cited

U.S. PATENT DOCUMENTS 4,782,819 A * 11/1988 Adair ........................ 600/178
5,274,611 A * 12/1993 Donohoe ..................... 368/10
5,589,742 A * 12/1996 Ueda ......................... 315/307
6,320,331 B1 * 11/2001 Iida et al. .................... 315/293

FOREIGN PATENT DOCUMENTS

JP  1-234812  *  9/1989  ............ A61B/1/06
JP  10-192238 *  7/1998  ............ A61B/1/06

* cited by examiner

*Primary Examiner*—John P. Leubecker
(74) *Attorney, Agent, or Firm*—Scully, Scott, Murphy & Presser

(57) ABSTRACT

An endoscope system has a lamp 22 that emits illumination light with which an object is illuminated, and a power supply 24 that supplies power with which the lamp is lit. Furthermore, the endoscope system includes a condition detecting unit and a notifying unit. The condition detecting unit is provided to or near the lamp 22 and detects a predetermined condition relevant to the lamp. The notifying unit notifies an operator of the state of the lamp according to a result of detection performed by the condition detecting unit. The condition detecting unit is a temperature detector 27 or a power detector 51. The temperature detector 27 detects whether the temperature at or near the lamp is equal to or larger than a predetermined value. The power detector 51 detects whether current or voltage supplied or applied from the power supply to the lamp is equal to or smaller than a predetermined value.

6 Claims, 22 Drawing Sheets

ENDOSCOPE DEVICE

This application claims benefit of Japanese Application No. 2000-138984 filed in Japan on May 11, 2000, and No. 2000-385620 filed in Japan on Dec. 19, 2000, the contents of which are incorporated by this reference.

BACKGROUND OF THE INVENTION

1. Field of the Invention

The present invention relates to an endoscope, and more particularly to an endoscope system having a lamp, which supplies illumination light to an illumination optical system for the purpose of observation, incorporated in an endoscope.

2. Description of the Related Art

Electronic endoscope systems are widely used in the medical field or in the industrial field alike. In particular, the electronic endoscope system used in the medical field has an elongated insertion member inserted into a patient's body cavity for the purpose of observation, diagnosis, or treatment of an organ. Various ideas have been implemented for fear that a patient's body may be damaged in case a malfunction occurs during use.

In a typical electronic endoscope system, a lamp incorporated in a light source apparatus is lit, and light emitted from the lamp is converged at an illumination light connector formed on an electronic endoscope (hereinafter an endoscope) using a condenser. The converged light is propagated into the distal part of the endoscope over a light guide that lies through the endoscope. Illumination light is then irradiated to an object through an illumination lens.

A view image of the object illuminated by the illumination light is projected on the imaging surface of a solid-state imaging device such as a CCD after passed through an observation lens located in the distal part of the endoscope. Power or a driving pulse is applied to the CCD incorporated in the distal part of the endoscope over a cable lying through an insertion member thereof. An image signal into which an optical image is photoelectrically converted by the CCD is converted into a video signal by a video processor that is an external apparatus, and outputted to a display device. Various data items including a date and a management serial number which are entered at a keyboard connected to the video processor is displayed together with an endoscopic view image on the screen of the display device.

The insertion member of the endoscope is inserted into a body cavity through the patient's mouth or anus. The thickness of the insertion member is restricted in consideration of inserting smoothness. Moreover, an amount of illumination light that is emitted to an object is attenuated to be smaller than an amount of light emitted from the lamp incorporated in the light source apparatus because of the properties of the light guide including the material thereof. Therefore, a large-power lamp is incorporated in the light source apparatus in order to supply an amount of light that is large enough to cause no obstacle to observation even if an amount of light gets attenuated.

In general, the large-power lamp dissipates a large amount of heat. Since the lamp is stowed in the housing of the light source apparatus that defines a closed space, the light source apparatus has a cooling means such as an air blower or a vent. Thus, the temperature in the housing is lowered to the temperature at which electronic circuits incorporated in the housing can operate normally.

However, if the air blower malfunctions or the vent is blocked due to some reason, cooling is not performed normally. The temperature in the housing of the light source apparatus rises to exceed the temperature stipulated in the specifications for the electronic endoscope system. Consequently, the electronic circuits may malfunction.

Therefore, a temperature detecting means is incorporated in the housing. If the temperature at the lamp or in the housing is equal to or larger than a predetermined value, the lamp is put out in order to prevent the temperature in the housing from exceeding the predetermined value.

Moreover, there is a fear that when the service life of the lamp has completed its span, the lamp incorporated in the light source apparatus may operate abnormally. As long as the lamp is a halogen lamp, the abnormality of the lamp stems from disconnection or deposition of a tungsten filament, and brings about a drop of current or voltage supplied or applied to the lamp. If the lamp exhibits such an abnormality, the lamp may be put out or may emit only a small amount of light. Consequently, since an amount of illumination light that is large enough to observe an object cannot be obtained, observation cannot be continued any longer.

According to a solution described in Japanese Unexamined Patent Publication No. 10-192238, a plurality of lamps is incorporated in a light source apparatus and the lamps other than a used lamp are put on standby. If a used lamp operates abnormally, the used lamp is changed to a standby lamp. The standby lamp is lit in order to continue observation.

However, when lamps are arranged to be interchangeable, after one lamp is changed to another lamp, the new lamp may not be located at a right position at which light emanating from the lamp is converged on a condenser. In this case, there arises a fear that light emanating from the lamp may not be fully converged on the condenser and an amount of illumination light that is large enough to observe an object may not be supplied.

Aside from the drawback that disables observation, there is a fear that the temperature at the lamp or in the housing of the light source apparatus may rise abnormally. This is because when a lamp to be lit is changed to another, the position of a heating source changes and cooling efficiency changes.

In efforts to overcome the drawbacks, a position-of-lamp detecting means may be included for sensing if a used lamp is located at a right position. If the position-of-lamp detecting means senses that a lamp is not located at a normal position, the lamp is put out in order to prevent the temperature at the lamp or in the housing of the light source apparatus from rising abnormally.

However, as far as the foregoing light source apparatus is concerned, if the lamp is put out, a user is unaware of the reason why the lamp is put out. Specifically, the lamp may be put out in order to prevent the temperature in the housing from rising because of a malfunction of a cooling means incorporated in the light source apparatus. The lamp may be put out or may emit only a small amount of light because the service life thereof has almost completed its span. Otherwise, since the lamp is not located at a normal position, illumination light is not converged on the condenser. For this reason, the lamp may emit only a small amount of light or may be put out. In either case, an operator lacks an amount of illumination light suitable for observation and cannot help suspending observation.

In efforts to lift the suspension, the operator peruses the operation manual for the endoscope system so as to understand why the lamp is put out or emits only a small amount of light. However, it is time-consuming to peruse the operation manual. This poses a problem in that prompt action cannot be taken and observation cannot be restarted immediately.

OBJECT OF THE INVENTION

The present invention attempts to break through the foregoing situation. An object of the present invention is to provide an endoscope system capable of notifying a user of the reason why a lamp is put out or emits only a small amount of light, and taking immediate measures to light the lamp normally.

SUMMARY OF THE INVENTION

According to the present invention, an endoscope system has a lamp that emits illumination light with which an object is illuminated, and a power supply means that supplies power with which the lamp is lit. The endoscope system includes a condition detecting means and a notifying means. The condition detecting means is provided to or near a lamp and detects a predetermined condition relevant to the lamp. Based on a result of detection performed by the condition detecting means, the notifying means notifies an operator of the state of the lamp.

More preferably, the condition detecting means is a temperature detecting means that detects whether the temperature at or near the lamp is equal to or larger a predetermined value. Otherwise, the condition detecting means is a power detecting means that detects whether current or voltage supplied or applied from the power supply means to the lamp is equal to or smaller than a predetermined value.

According to the foregoing components, the notifying means notifies a user of the state of the lamp detected by the temperature detecting means or power detecting means. The user can therefor take prompt action.

DESCRIPTION OF THE PREFERRED EMBODIMENTS

Figure 1:
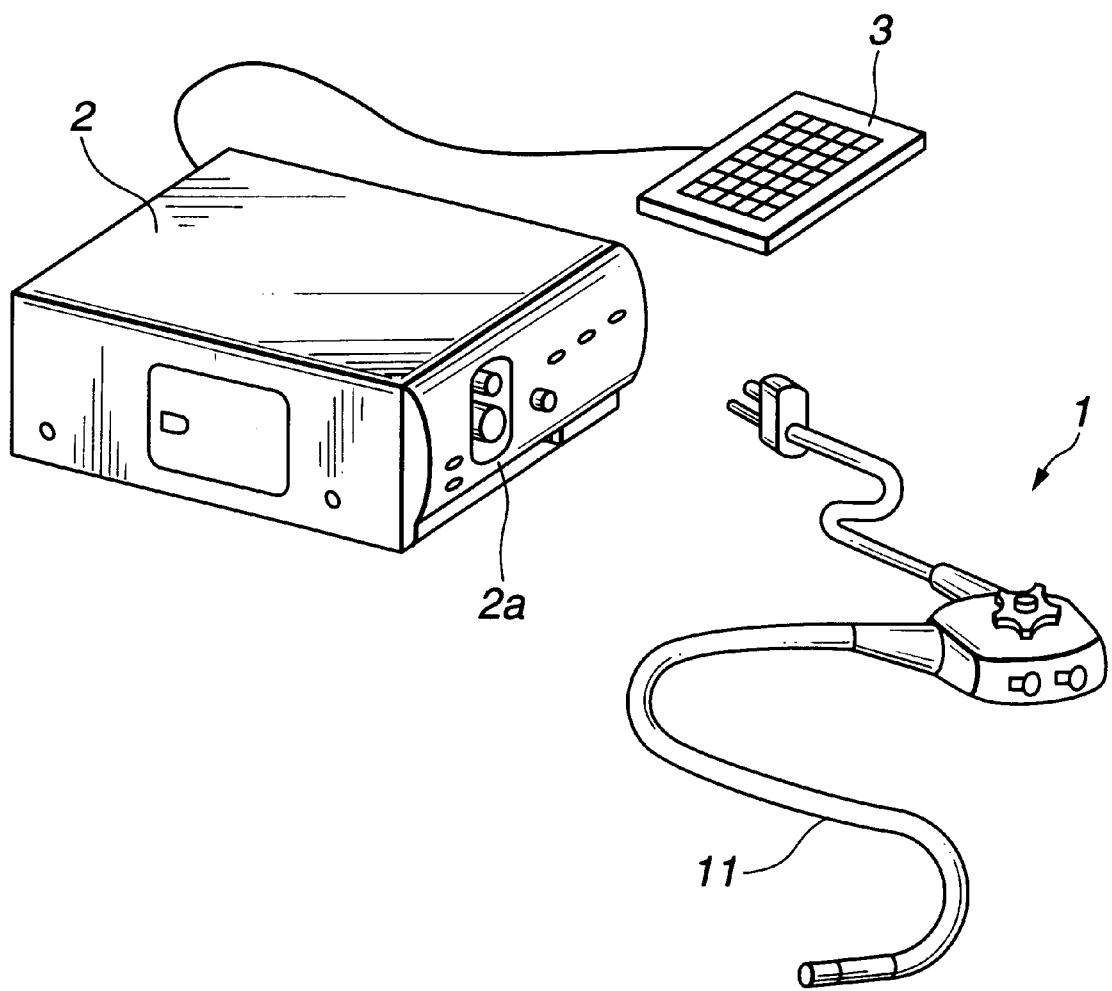
FIG. 1 is an explanatory diagram explaining the configuration of an electronic endoscope system.

Referring to the drawings, embodiments of the present invention will be described below.

Figure 2:
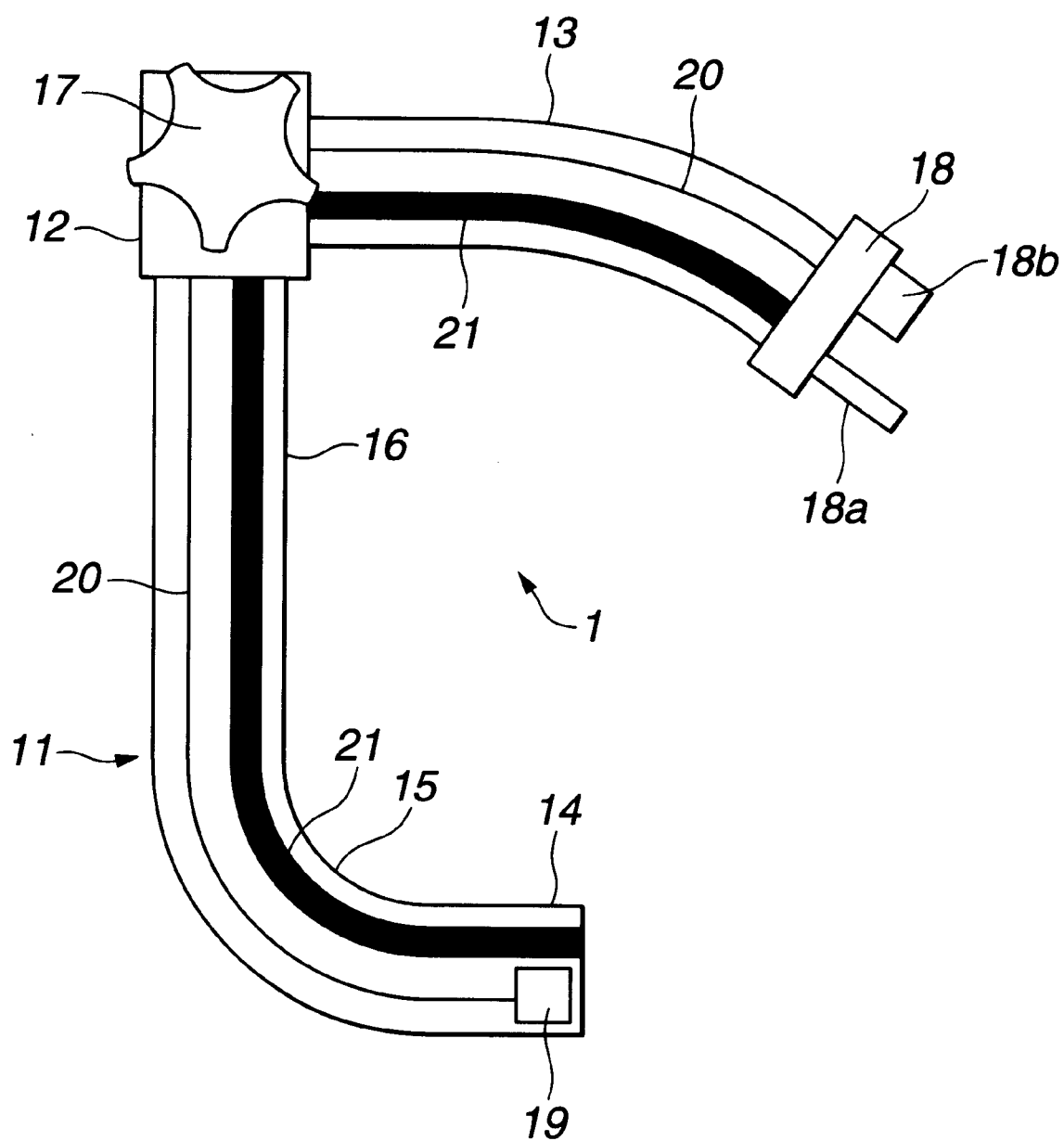
FIG. 2 is an explanatory diagram showing the components of an electronic endoscope.
Figure 3:
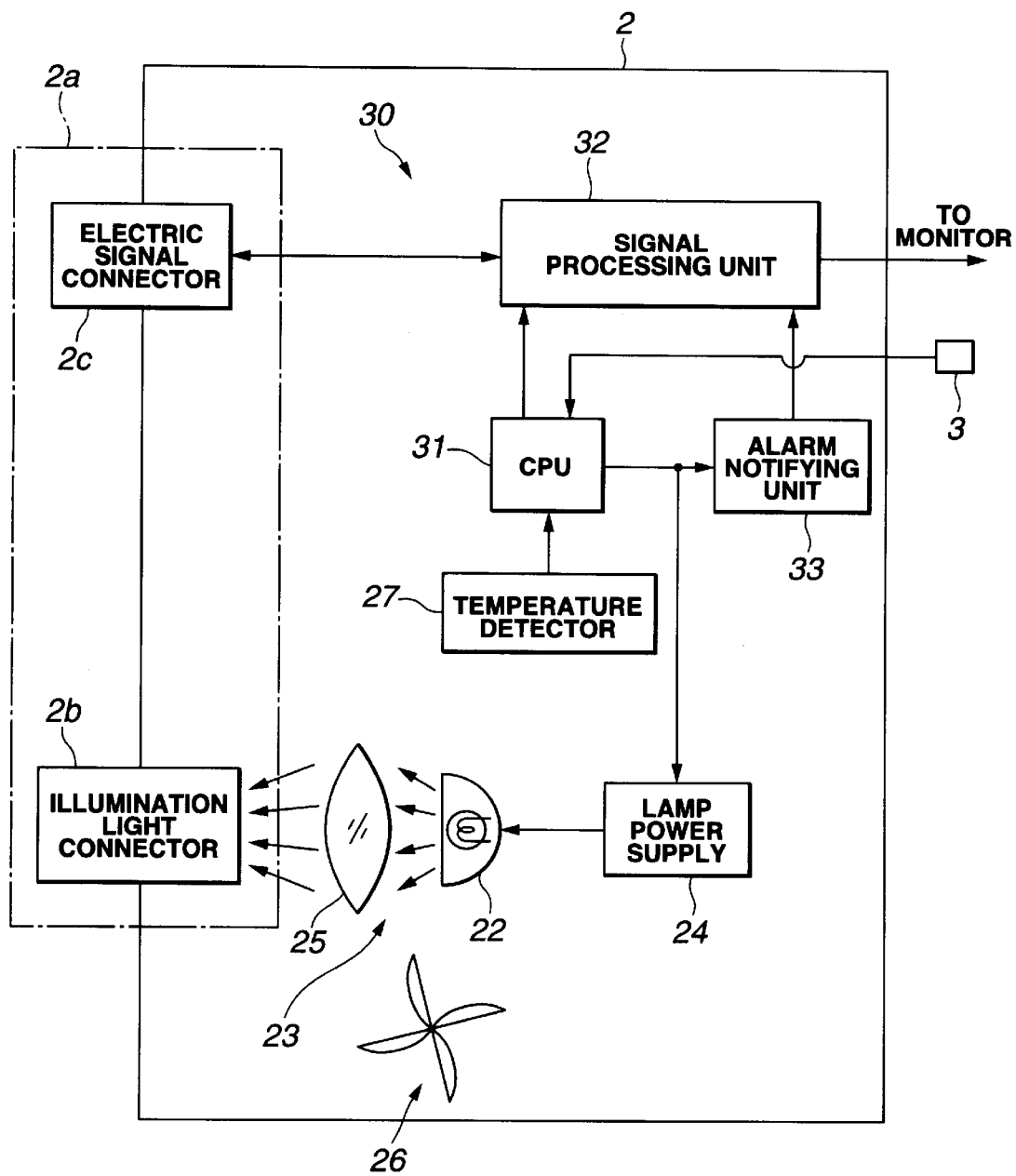
FIG. 3 is an explanatory block diagram showing the configuration of a main apparatus of the endoscope system.
Figure 4:
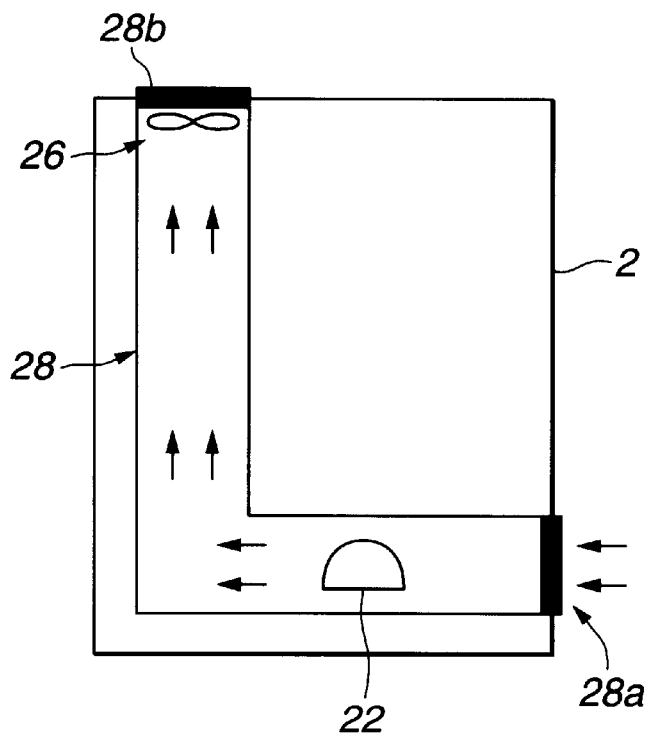
FIG. 4 is an explanatory diagram showing the positional relationship between a lamp and a cooling channel used to cool the air around the lamp incorporated in the main apparatus of the endoscope system.
Figure 5:
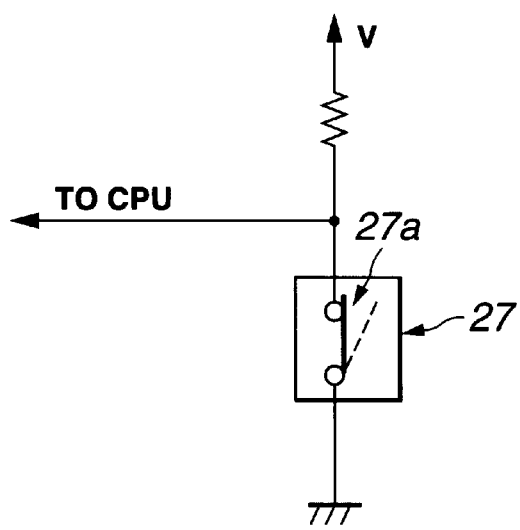
FIG. 5 is an explanatory diagram showing the action of a selector switch that selects connection to a temperature detector.
Figure 6:
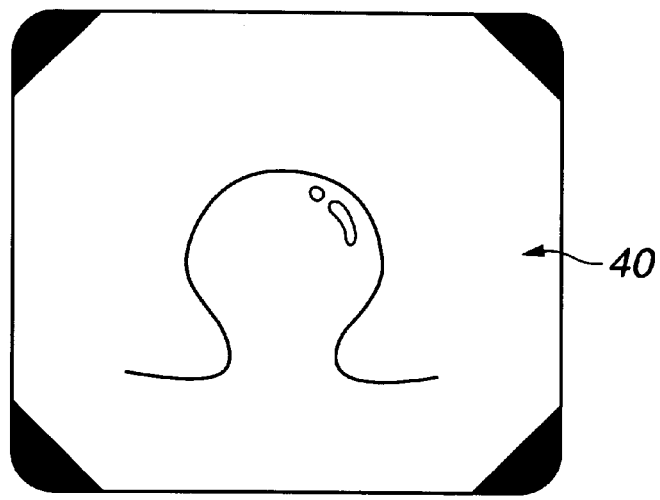
FIG. 6 shows an example of an endoscopic view image.
Figure 7:
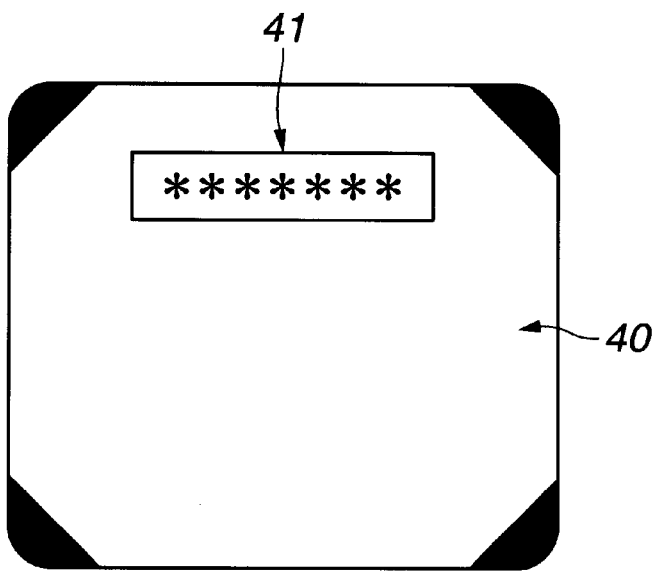
FIG. 7 shows an example of an endoscopic view image with a notifying message displayed together.

FIG. 1 to FIG. 7 are explanatory diagrams concerning a first embodiment of the present invention. FIG. 1 is an explanatory diagram explaining the configuration of an electronic endoscope system. FIG. 2 is an explanatory diagram showing the components of an electronic endoscope. FIG. 3 is an explanatory block diagram showing the configuration of a main apparatus of the endoscope system. FIG. 4 is an explanatory diagram showing the positional relationship between a lamp and a cooling channel used to cool the air around the lamp incorporated in the main apparatus of the endoscope system. FIG. 5 is an explanatory diagram showing the action of a selector switch that selects connection to a temperature detector. FIG. 6 shows an example of an endoscopic view image. FIG. 7 shows an endoscopic view image with a notifying message displayed together.

As shown in FIG. 1, an electronic endoscope system in accordance with the present embodiment comprises an electronic endoscope (hereinafter, simply, an endoscope) 1, a main apparatus 2, and a keyboard 3. The endoscope 1 has a solid-state imaging device such as a CCD incorporated in an insertion member 11 thereof that is inserted into a patient's body cavity for the purpose of observation. The main apparatus 2 has a processor and a light source unit incorporated in, for example, a housing thereof. The processor converts an image signal sent from the CCD incorporated in the insertion member 11 into a video signal, or displays a view image or various data items on a monitor (not shown). The light source unit includes a lamp, which will be described later, for supplying illumination light to the endoscope 1. The keyboard 3 is connected to the main apparatus 2 and used to enter characters or numerals that signify patient data or observation data.

As shown in FIG. 1 and FIG. 2, the endoscope 1 comprises an elongated insertion member 11, an operation unit 12, and a universal cord 13. The operation unit 12 is coupled to the proximal end of the insertion member 11, and the universal cord 13 is extended from the lateral part of the operation unit 12.

The insertion member 11 has a distal structure 14, a bending section 15, and a flexible tube 16 concatenated in that order from the distal end thereof. The distal structure 14 is a rigid portion. The bending section 15 can be freely bent. The flexible tube 16 is flexible. The operation unit 12 has an angling knob 17 that is manipulated to bend the bending section 15. An endoscope connector 18 composed of an illumination connector 18a and a signal connector 18b is fixed to the proximal end of the universal cord 13. The endoscope connector 18 is joined to a system connector 2a formed in the main apparatus 2 so that it can be joined and disjoined freely. Illumination light is propagated through the illumination connector 18a, and an electric signal is outputted or inputted through the signal connector 18b.

The CCD 19 that photoelectrically converts an optical image of an object to be observed into an image signal is incorporated in the distal structure 14 of the insertion member 11. A signal cable 20 extended from the CCD 19 to the signal connector 18b of the endoscope connector 18 lies through the insertion unit 11, operation unit 12, and universal cord 13. Moreover, a light guide 21 over which light emitted from a lamp incorporated in the main apparatus 2 is propagated as illumination light, which is radiated in a patient's body cavity, lies through the insertion member 11, operation unit 12, and universal cord 13.

As shown in FIG. 3, a light source unit 23 and a processor 30 are incorporated in the main apparatus 2. The light source unit has a lamp 22 and supplies illumination light over the light guide 21. The processor 30 executes various control sequences so as to generate a video signal according to an image signal sent from the CCD 19 or display a view image and various data items on a monitor.

Moreover, the system connector 2a of the main apparatus 2 is composed of an illumination light connector 2b and an electric signal connector 2c that are connected to the light source unit 23 and processor 30 respectively.

The light source unit 23 comprises the lamp 22, a lamp power supply 24, a condenser 25, a cooling fan 26, and a temperature detector 27. The lamp 22 generates illumination light. The lamp power supply 24 is a power supply means for supplying power to the lamp 22. The condenser 25 converges light, which is emitted from the lamp 22, on the end surface of the illumination connector 18a of the endoscope connector 18 that is mated with the illumination light connector 2b of the system connector 2a. The cooling fan 26 discharges heat, which is dissipated from the lamp 22, to the outside of the housing of the main apparatus, whereby the temperature at or near the lamp 22 is prevented from rising. The temperature detector 27 serves as a condition detecting means and is located near the lamp 22. The temperature detector 27 is, in a narrow sense, a temperature detecting means that detects whether the temperature at or near the lamp is equal to or larger than a predetermined value. When the temperature detector 27 detects that the temperature at or near the lamp is equal to or larger than a predetermined value, it performs predetermined switching.

As shown in FIG. 4, a cooling channel 28 having an intake port 28a and an exhaust port 28b is formed in the main apparatus 2. Air is taken in through the intake port 28a for the purpose of cooling. The cooling fan 26 is located near the exhaust port 28b so that air heated while drifting near the lamp can be exhausted through the exhaust port 28b.

As shown in FIG. 5, when the temperature near the lamp is equal to or smaller than a predetermined value (hereinafter, the temperature will be referred to as normal temperature), a selector switch 27a included in the temperature detector 27 is closed as indicated with a solid line. When the temperature near the lamp is equal to or larger than the predetermined value (hereinafter the temperature will be referred to as abnormal temperature), the selector switch 27a is opened. Thus, the temperature detector 27 outputs a sense signal to the CPU 31. Specifically, when the normal temperature is detected as shown in FIG. 5, a low-level signal is outputted to the CPU. When the abnormal temperature is detected, a high-level signal is outputted thereto.

The processor 30 comprises the CPU 31, a signal processing unit 32, and an alarm notifying unit 33 which is a notifying means. The CPU 31 controls lighting of the lamp 22, and holds patient data, a date, a management serial number, and other data which are entered at the keyboard 3. The signal processing unit 32 is connected to the electric signal connector 2c of the system connector 2a with which the endoscope connector 18 is mated. The signal processing unit 32 supplies power or a driving pulse to the CCD 19, and receives an image signal from the CCD 19, converts the image signal into a video signal, and outputs the video signal to the display device. Moreover, the signal processing unit 32 displays the date and management serial number, which are entered at the keyboard 3, on the screen of the display device. The alarm notifying unit 33 is a notifying means that when the temperature detector 27 detects the abnormal temperature, and notifies a user of the fact that the abnormal temperature has been detected when instructed by the CPU 31.

Operations to be exerted by the main apparatus 2 having the foregoing components will be described below.

When the lamp 22 incorporated in the main apparatus 2 is lit, light emitted from the lamp 22 is converged on the end surface of the illumination connector 18a mated with the illumination light connector 2b through the condenser 25. At the same time, the cooling fan 26 starts rotating.

Light converged on the illumination connector 18a is propagated over the light guide 21, and radiated forwards as illumination light from the distal structure 14 of the insertion member 11.

When the lamp 22 is kept lit, the temperature at the lamp 22 rises, and the temperature near the lamp also rises. At this time, since the lamp 22 is located in the cooling channel 28 that has the intake port 28a and exhaust port 28b, air heated while drifting near the lamp is exhausted to outside from the exhaust port 28b with the cooling fan 26. Moreover, outside air enters through, the intake port 28a to drift near the lamp, thus cooling the lamp. Consequently, the temperature inside the main apparatus 2 is retained at the normal temperature but will not rise to cause electronic circuits incorporated in the main apparatus 2 to malfunction or fail.

At this time, the temperature detector 27 closes the selector switch 27a because the temperature near the lamp is held normal, and outputs a low-level signal to the CPU 31. The CPU 31 having inputted the low-level signal does not generate a control signal that prompts the alarm notifying unit 33 to alarm an operator.

A view image of an intracavitary region illuminated with illumination light is projected on the imaging surface of the CCD 19 that is driven with power or a driving pulse supplied or applied from the signal processing unit 32. The image is then photoelectrically converted into an image signal. The image signal is inputted to the signal processing unit 32 over the signal cable 20 via the signal connector 18b and electric signal connector 2c.

The image signal transferred from the CCD 19 to the signal processing unit 32 is subjected to noise minimization such as correlative double sampling, and gain control, and then outputted as a video signal together with data held in the CPU 31 to a monitor that is an external apparatus. Consequently, an endoscopic view image is, as shown in FIG. 6, displayed on a screen 40 of the display device.

During endoscopic observation, the intake port 28a or exhaust port 28b, or the middle point of the cooling channel 28 may be blocked due to some reason. Otherwise, the cooling fan 26 may fail to operate normally. In this case, cooling is achieved insufficiently and the temperature near the lamp rises.

If the temperature at or near the lamp is equal to or larger than a predetermined value, the temperature detector 27 reacts to the abnormal temperature, or in other words, detects the abnormal temperature. The temperature detector 27 then changes the selector switch 27a from the closed state to the open state. Consequently, the signal outputted from the temperature detector 27 to the CPU 31 makes a low-to-high transition.

In response to the high-level signal, the CPU 31 controls the lamp power supply 24 so as to prevent a temperature rise, and stops supply of power to the lamp 22 so as to put out the lamp 22. Moreover, the CPU 31 outputs a control signal that prompts the alarm notifying unit 33 to alarm an operator. Consequently, the alarm notifying unit 33 performs notification to inform an operator of the fact that the lamp 22 is put out because the temperature in the housing is abnormal.

Specifically, the CPU 31 not only puts out the lamp 22 but also instructs the alarm notifying unit 33 to perform notification. That is to say, the CPU 31 instructs the alarm notifying unit 33 to display a predetermined message or a predetermined mark or symbol (not shown) in a message display field 41 so as to notify an operator of the fact that an abnormality has occurred. At this time, the predetermined message, mark, or symbol is superimposed on an endoscopic view image. Iteratively, the predetermined message, mark, or symbol is displayed in order to inform an operator of the fact that the lamp is put out because of the abnormal temperature. The means for alarming an operator is not limited to displaying of the message, mark, or symbol but may be generation of a predetermined sound using a buzzer or the like. In this case, a sound control means is included in the alarm notifying unit 33.

When the lamp 22 is put out, a heat source disappears. Consequently, the temperature at or near the lamp 22 drops gradually, and the failure of the electronic circuits is avoided.

As mentioned above, the temperature detector for detecting whether the temperature at or near the lamp is equal to or larger than a predetermined value is provided near the lamp, which is a heat source, in the main apparatus. Moreover, the alarm notifying unit is included for alarming an operator of the abnormal temperature when the abnormal temperature is detected. If cooling the interior of the main apparatus should fail, the temperature at or near the lamp may be equal to or larger than the predetermined value. In this case, the temperature detector outputs a sense signal to the CPU. Consequently, the lamp is put out in order to prevent a further rise of temperature. Besides, an operator is immediately notified of the reason why the lamp is put out.

Consequently, the notified operator takes prompt action to cope with the failure to cool the interior of the main apparatus, and proceeds with examination.

According to the present embodiment, when the CPU 31 receives a high-level signal from the temperature detector 27, the CPU 31 puts out the lamp 22, and instructs the alarm notifying unit 33 to perform notification. Alternatively, when the CPU 31 receives the high-level signal from the temperature detector 27, the CPU 31 may first instruct the alarm notifying unit 33 to perform notification. Thereafter, the CPU 31 may reduce an amount of light emanating from the lamp to such an extent that observation will not be obstructed, or may keep the lamp 22 lit until a certain time elapses or until the fear that the electronic circuits may malfunction is eliminated. A solution program that describes instructions to be followed by the CPU may be installed in, advance in the CPU 31. In this case, when the temperature in the housing rises to be the abnormal temperature, before the lamp is put out, an operator can immediately remove the insertion member 11 from a body cavity while looking at an endoscopic view image. Thereafter, the operator can take much time to cope with the failure to cool the interior of the main apparatus.

Thereafter, the processor incorporated in the endoscope system in accordance with the first embodiment will be described in conjunction with a more detailed circuit block diagram.

Figure 8:
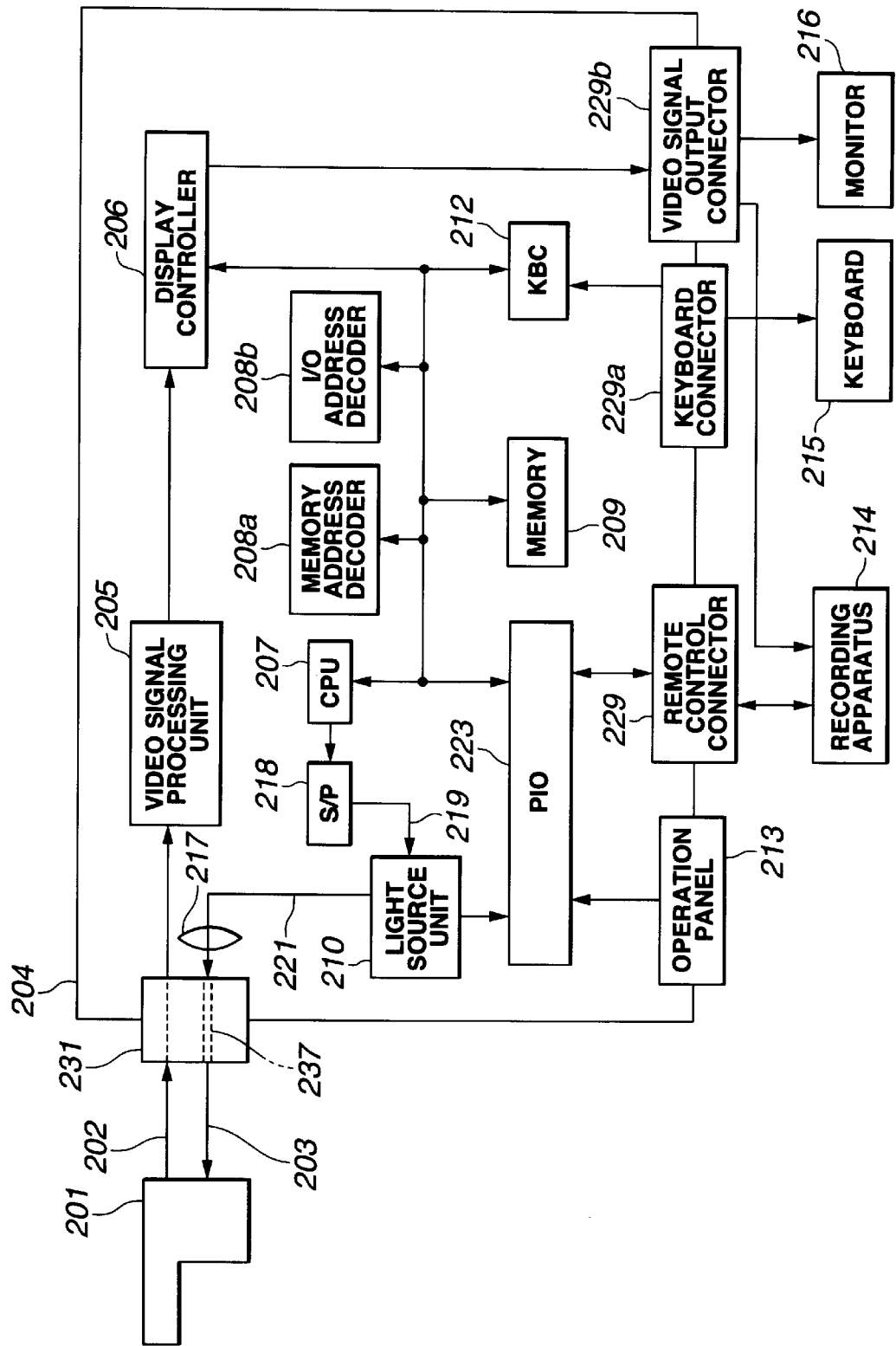
FIG. 8 is a block diagram showing the overall configuration of the endoscope system.

FIG. 8 is a block diagram showing the overall configuration of the endoscope system.

An endoscope 201 outputs an endoscopic image (video signal) of an object imaged by a CCD (not shown) incorporated in the distal part of the endoscope to a processor 204 over a video signal cable 202. The processor 204 performs various kinds of video signal processing and controls the system. The endoscope 201 and processor 204 are connected to each other via an endoscope connector 231.

The processor 204 includes a CPU 207, a memory 209, an address/data bus (not shown), a memory address decoder 208a, an I/O address decoder 208b, an I/O port (PIO) 223, a display controller 206, a keyboard controller (KBC) 212, a light source unit 210, a video signal processing unit 205, an operation panel 213, a remote control connector 229, a video signal output connector 229b, and a keyboard connector 229a. The display controller 206 renders characters. The keyboard controller 212 controls the keyboard. The video signal processing unit 205 performs digitization, color correction, contour enhancement, white balance control, and other processing on a video signal sent from the endoscope 201. The remote control connector 229 is used to connect the processor to any of various recording apparatuses. The video signal output connector 229b is used to connect the processor to the monitor. The keyboard connector 229a is used to connect the processor to a keyboard. A recording apparatus 214 that records endoscopic image data, a monitor 216 on which an endoscopic image is displayed, and a keyboard 215 at which various data items are entered or the system is controlled are plugged in to the connectors.

The light source unit 210 supplies illumination light required to observe a region to be observed. The light source unit 210 includes a lamp 227, a lamp power supply 228, a lamp cooling fan 230, and some abnormality-of-lamp detecting means. Light 221 emitted from the lamp in the light source unit 210 is passed through a condenser 217, introduced into a light path hole 237 in the endoscope connector 231, and then propagated to the distal part of the endoscope 201 over a light guide 203. The light source unit 210 is controlled by the CPU.

Moreover, an endoscopic image represented by a video signal on which various kinds of video signal processing are performed by the video signal processing unit 205 is transferred to the display controller 206. The display of various messages on the endoscopic image. The resultant image is outputted to the monitor 216 or recording apparatus 214 via a video signal output connector. The display controller 206 is controlled by the CPU 207.

Figure 9:
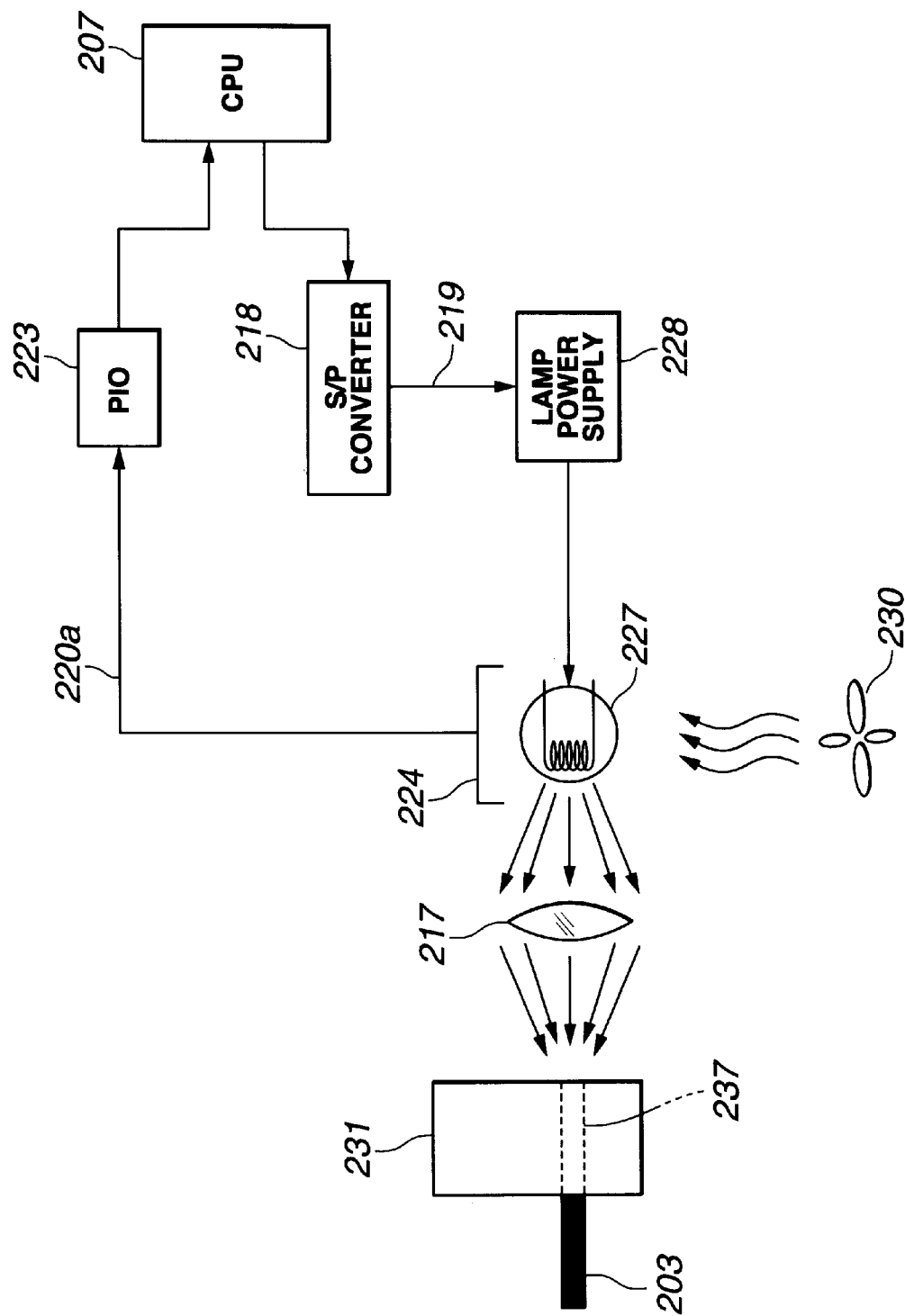
FIG. 9 shows the concrete configuration of a light source unit shown in FIG. 8.

In order to properly control lighting of the lamp, measures must be taken on the assumption that the light source unit 210 may malfunction. Measures to be taken when the temperature at the lamp is abnormal (the lamp is overheated) will be described in conjunction with FIG. 9. FIG. 9 shows the concrete configuration of the light source unit 210 shown in FIG. 8.

A serial signal containing a lighting control signal, which prompts lighting or putting out of the lamp 227, is outputted from the CPU 207 to a serial-to-parallel (SIP) converter 218. After the S/P converter 218 converts the serial signal into a parallel signal, a lamp lighting control signal 219 is outputted to the lamp power supply 228 in order to control lighting of the lamp 227. When the lamp 227 is lit, light emitted from the lamp is passed through the condenser 217, introduced into the light path hole 37 of the endoscope connector 231, and irradiated from the distal end of the endoscope 201 over the light guide 203. The lamp 227 is cooled using the lamp cooling fan 230 in order to prevent the temperature at or around the lamp 227 from rising abnormally.

However, the lamp cooling fan 230 may fail or the temperature at or around the lamp 227 may rise abnormally to such an extent that the temperature surpasses the cooling ability of the lamp cooling fan 230. In this case, there arises a fear that the filament of the lamp 227 may be fused or the circuits around the lamp may be broken.

Therefore, a lamp temperature detector 224 is located near the lamp 227 in order to monitor the temperature at and around the lamp 227 all the time while the lamp 227 is lit. If the temperature at the lamp 27 exceeds a specific value, a lamp temperature error signal 220a is outputted through the I/O port 223. The lamp temperature error is transmitted to the CPU 207. When the CPU 207 senses the lamp temperature error, the CPU 207 instructs the display controller 206 to display an alarm message, which alarms a user of the lamp temperature error, on the monitor 216. Thus, occurrence of an abnormality is visually notified using the monitor 16. The user can be aware of the fact that the system operates abnormally and can take prompt action.

If the temperature at the lamp is abnormal, there arises a fear that the filament of the lamp may be fused or the circuits may be broken. In this case, preferably, the use of the system should be immediately suspended and the power supply should be immediately turned off. Therefore, if the temperature at the lamp is abnormal, the CPU 207 may ignore information that is transmitted to the CPU 207 through the I/O port 223 responsively to a manipulation performed on the operation panel 213 (for example, turning on or off of a pump or switching of light adjustment modes). Thus, the CPU 207 may persuade a user to suspend the use of the system immediately. Furthermore, when a certain time (for example, 60 sec) has elapsed since the temperature at the lamp became abnormal, the lamp 227 may be forcibly put out in order to thus prevent fusion of the filament or breakage of the circuits.

As mentioned above, the lamp temperature error signal 220a is transmitted to the CPU 207 through the I/O port 223 (using a parallel signal). The lamp lighting control signal 219 is transmitted to the lamp power supply 228 via the S/P converter 218 (using a serial signal). Alternatively, the serial signal may be used as the lamp temperature error signal 220a, and the parallel signal may be used as the lamp lighting control signal 219. Otherwise, the serial signals or parallel signals may be used as both the lamp temperature error signal 220a and lamp lighting control signal 219.

Moreover, the means for alarming a user of the fact that the temperature at the lamp is abnormal is not limited to displaying of a message on the monitor 216. Alternatively, the means may be visual alarming to be performed using an alarming LED included in the operation panel, acoustic alarming to be performed using an acoustic alarming means such as a buzzer, or a combination of these means.

Figure 10:
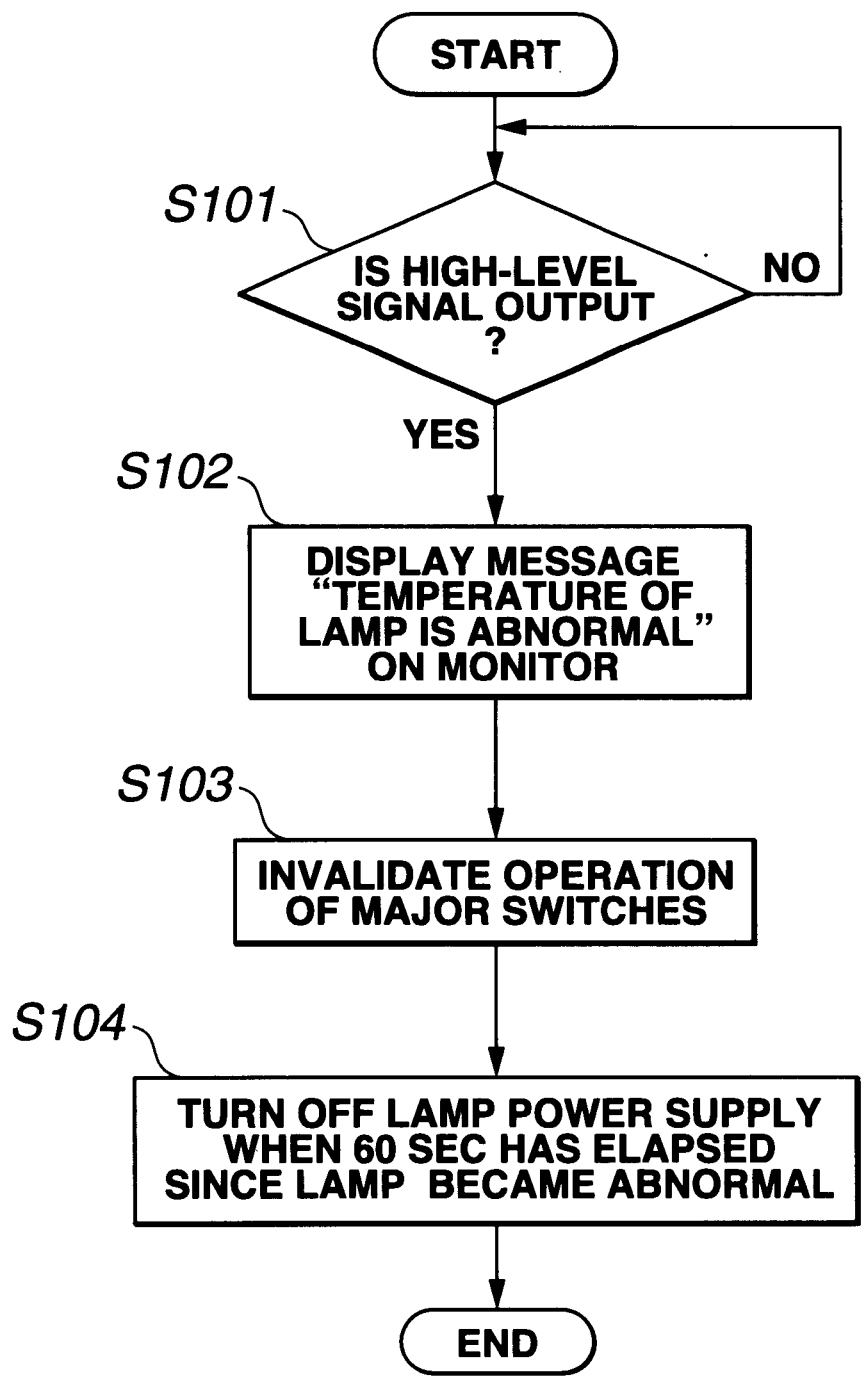
FIG. 10 is a flowchart describing processing to be performed by a CPU when the temperature at a lamp is abnormal.

FIG. 10 is a flowchart describing processing to be performed by the CPU when the temperature at the lamp is abnormal.

After the power supply is turned on, a low-level signal is outputted as the lamp temperature error signal 220a from the lamp temperature detector 224 through the I/O port 223. Since the lamp temperature error signal 220a is active high, immediately after the power supply is turned on, the lamp temperature error signal 220a is driven low in order to reset abnormal lamp temperature detection. After the lamp temperature error signal 220a is driven low, the lamp temperature detector 224 starts detecting the temperature at the lamp. If it is found as a result of detection that the temperature at the lamp is equal to or smaller than a predetermined value (that is, falls within a range of proper temperature values), a low-level signal is outputted as the lamp temperature error signal 220a. Detecting the temperature at the lamp is continued thereafter. Unless the temperature at the lamp is abnormal, detecting the temperature at the lamp is continuously performed all the time.

On the other hand, if the temperature at the lamp is equal to or larger than the predetermined value (that is, the temperature is abnormal), the lamp temperature detector 224 outputs a high-level signal as the lamp temperature error signal 220a through the I/O port 223. When the high-level signal is supplied to the CPU 207, a judgment is made affirmatively at step S101. The CPU 207 instructs the display controller 206 to display a message "The lamp temperature is abnormal" on the monitor 216 (S102). If the temperature at the lamp is abnormal, signals assigned to the pins of the I/O port 223 and transmitted to the CPU 207 responsively to manipulations performed on the operation panel 13 are invalidated (S103). Furthermore, when sixty seconds has elapsed since the temperature at the lamp became abnormal, the CPU 207 forcibly turns off the lamp power supply 228 (S104) so as to put out the lamp 27. This causes the temperature at the lamp 27 that is abnormally overheated to drop. Consequently, fusion of the filament or breakage of circuits can be avoided.

After the power supply is turned on, analog-digital conversion for a temperature signal sent from the lamp temperature detector may be carried out and the converted signal is supplied to the CPU 207. The CPU 207 may then detect whether the temperature has exceeded the predetermined value.

Figure 11:
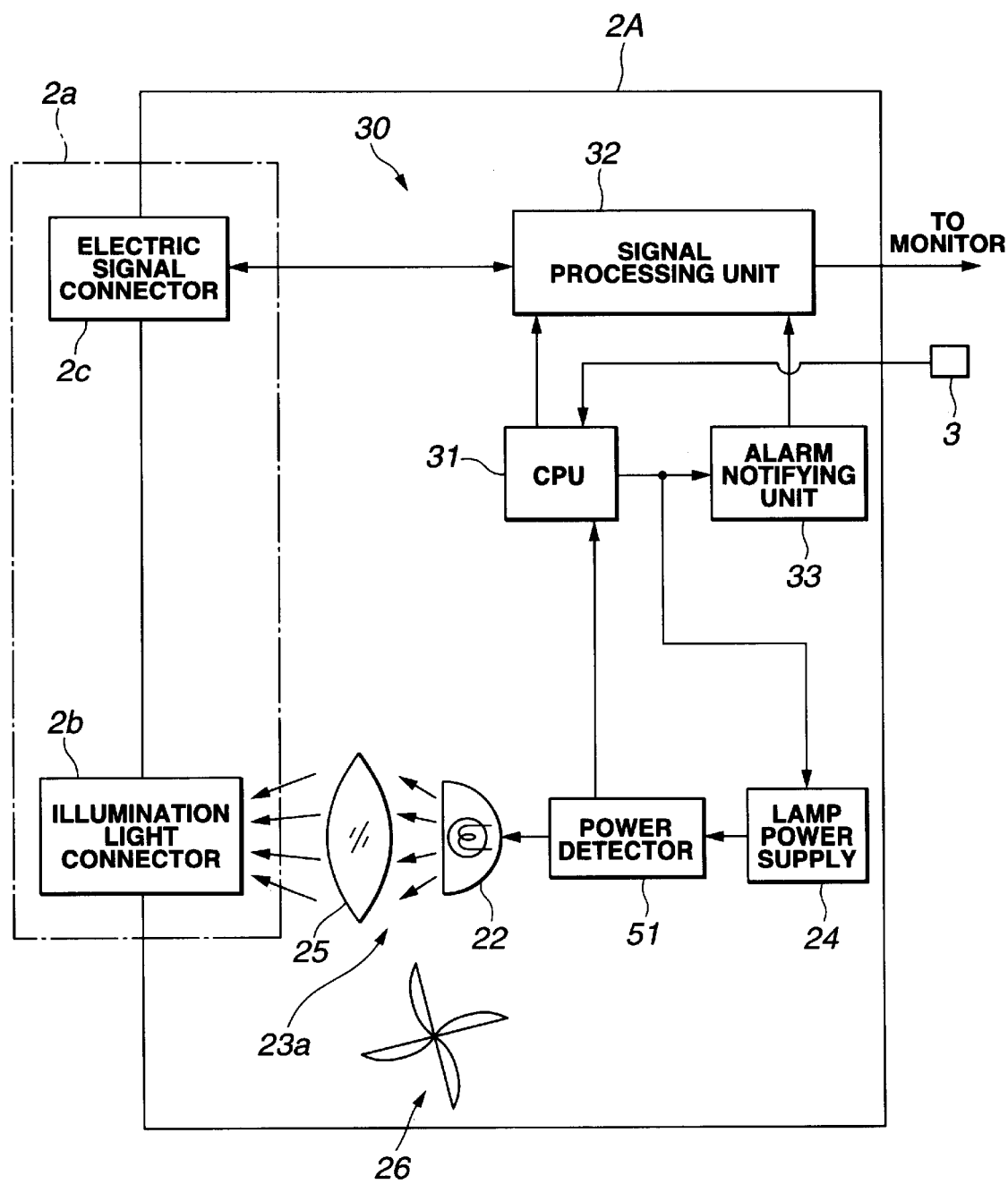
FIG. 11 is an explanatory block diagram showing the configuration of a main apparatus of an endoscope system in accordance with a second embodiment of the present invention.
Figure 12:
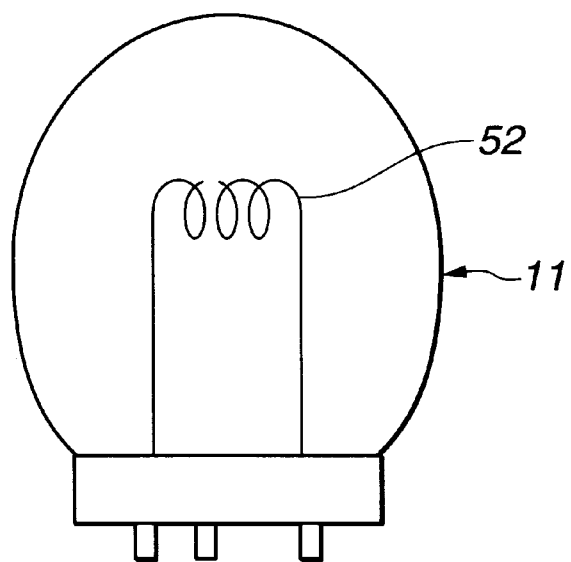
FIG. 12 is an explanatory diagram showing a lamp whose tungsten filament is fused.
Figure 13:
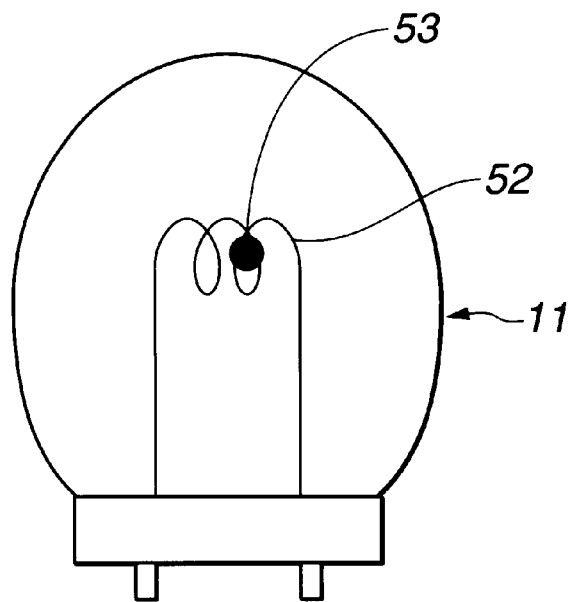
FIG. 13 shows a lamp whose tungsten filament has part thereof deposited.

Next, a second embodiment will be described below. FIG. 11 to FIG. 13 are explanatory diagrams showing the second embodiment of the present invention. FIG. 11 is a block diagram showing the configuration of a main apparatus of an endoscope system. FIG. 12 is an explanatory diagram showing a lamp whose tungsten filament is fused. FIG. 13 is an explanatory diagram showing the lamp whose tungsten filament has part thereof deposited.

As shown in the figure, a light source unit 23a incorporated in a main apparatus 2A of an endoscope system in accordance with the present embodiment has a power detector 51 located near the lamp 22. The power detector 51 that is a power detecting means is adopted as a condition detecting means on behalf of the temperature detector 27 employed in the first embodiment.

When the power detector 51 detects that voltage or current applied or supplied from the lamp power supply 24 to the lamp 22 is equal to or smaller than a predetermined value (hereinafter this state may be referred to as that the lamp operates abnormally), the power, detector 51 activates a selector switch (not shown) included therein in the same manner as the temperature detector 27 does. The power detector 51 then outputs a sense signal to the CPU 31. Specifically, when the lamp operates normally, even the power detector 51 transmits a low-level signal to the CPU 31. When the lamp operates abnormally, the power detector 51 outputs a high-level signal to the CPU 31. The other components are identical to those of the first embodiment. The same reference numerals will be assigned to the same components, and the description of the components will be omitted.

Operations to be exerted by the main apparatus 2A having the foregoing components will be described below.

When power is supplied to the lamp 22 incorporated in the main apparatus 2A, the power detector 51 detects the state of the lamp 22. If it is detected that the lamp does not operate abnormally, a low-level signal is outputted to the CPU 31. Consequently, the CPU 31 controls the lamp power supply 24 so as to light the lamp 22.

Light emitted from the lamp 22 is passed through the condenser 25, converged on the end surface of the illumination connector 18a mated with the illumination light connector 2b, propagated over the light guide 21, and radiated forwards as illumination light from the distal structure 14 of the insertion member 11.

However, the time during which the lamp 22 can be lit is limited, that is, the service life of the lamp 22 completes its span in due course. Therefore, when observation is continuously performed with the lamp 22 lit, the lamp 22 will complete its span without fail.

Assuming that the lamp 22 is a halogen lamp, when the service life of the lamp 22 has almost completed its span, the tungsten filament 52 is fused. The lamp 22 is opened and does not conduct electricity. The lamp 22 is therefore not lit.

Otherwise, after the tungsten filament 52 is fused, a deposited part 53 is formed as shown in FIG. 10. At this time, the resistance offered by the tungsten filament 52 decreases. Voltage applied to the lamp 22 is therefore smaller than a right value. This leads to a decrease in an amount of light emanating from the lamp 22.

In other words, when the tungsten filament 52 is fused or the deposited part 53 is formed, current or voltage supplied or applied to the lamp 22 decreases. At this time, the power detector 51 senses that the lamp operates abnormally, and changes the signal to be outputted to the CPU 31 from a low-level signal to a high-level signal which indicates that the lamp operates abnormally.

In response to the high-level signal, the CPU 31 outputs a control signal that prompts the alarm notifying unit 33 to alarm an operator. Consequently, the alarm notifying unit 33 performs notification to alarm an operator of the fact that since the lamp operates abnormally, the lamp 22 is put out or produces only a small amount of light.

The CPU 31 puts out the lamp 22. At the same time, the CPU 31 instructs the alarm notifying unit 33 to perform notification. Specifically, a predetermined message, mark, symbol (not shown), or the like is, as shown in FIG. 7, superimposed on an endoscopic image so that it will be displayed in the message display field 41. This is intended to inform the operator of the fact that since the lamp operates abnormally, the lamp 22 is put out or produces only a small amount of light. Thus, the operator is notified of the fact that an abnormality has occurred. The notifying means is not limited to displaying of the message, mark, or symbol, but may be generation of a predetermined sound using a buzzer or the like. Thus, the buzzer may be used in order to alarm the operator. In this case, a sound control means is included in the alarm notifying unit 33.

As mentioned above, the power detector for detecting if the lamp operates abnormally is provided in the main apparatus. Besides, the alarm notifying unit for notifying an operator of the fact that the lamp operates abnormally is included therein. If the lamp should operate abnormally, the lamp would be put out or produce only a small amount of light. Nevertheless, the operator is immediately notified of the reason why the lamp is put out or produces only a small amount of light.

Consequently, the notified operator replaces the lamp with a new one and proceeds with examination.

Figure 14:
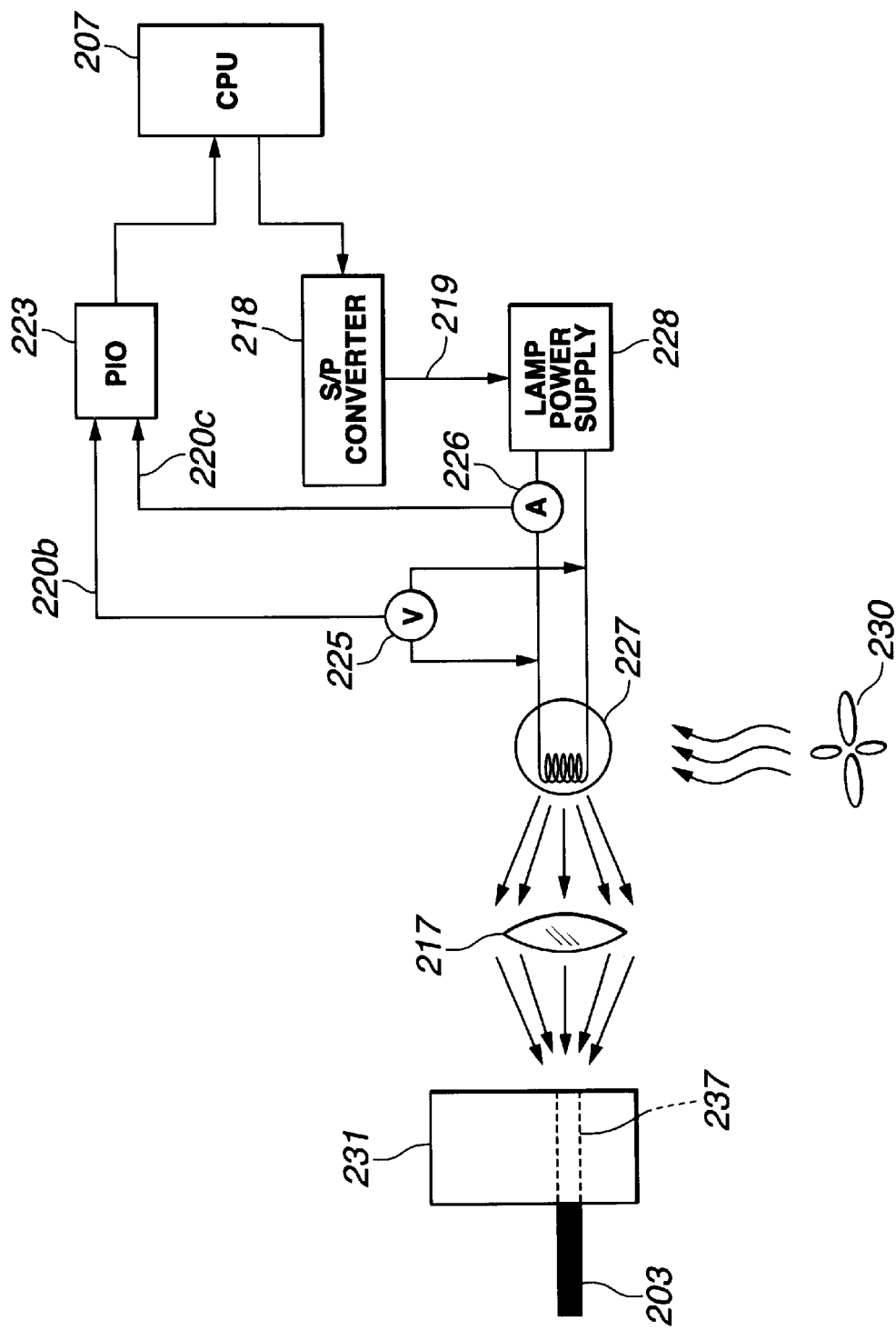
FIG. 14 shows the concrete configuration of a light source unit included in the endoscope system in accordance with the second embodiment.

Next, the light source unit included in the endoscope system in accordance with the second embodiment will be detailed below. FIG. 14 shows the concrete configuration of the light source unit included in the endoscope system in accordance with the second embodiment. The other components are identical to those of the first embodiment. The same reference numerals will be assigned to components identical to those shown in FIG. 8 and FIG. 9, and the description of the components will be omitted.

Measures to be taken when current or voltage supplied or applied to the lamp is abnormal will be described in conjunction with FIG. 14. FIG. 14 shows the concrete configuration of the light source unit 210 shown in FIG. 8. The same reference numerals will be assigned to components identical to those of the first embodiment, and the description of the components will be omitted.

The filament of the lamp 227 may be fused when the service life of the lamp 227 has almost completed its span. Otherwise, the filament may be partly deposited immediately after fused. In the former case, since no current flows into the filament, the lamp 227 is not lit (current-related abnormality). In the latter case, current flows but the resistance offered by the filament decreases. Therefore, voltage to be applied to the lamp drops, and a sufficient amount of light is not emitted from the lamp (voltage-related abnormality). If either the current-related or voltage-related abnormality occurs, observation cannot be achieved properly. A user who is an operator must be notified of the fact.

Current and voltage supplied or applied to the lamp 227 are monitored all the time. In other words, when the current-related abnormality occurs, a lamp current detector 226 detects the current-related abnormality, and outputs a lamp current error signal 220c to the I/O port 223. When the voltage-related abnormality occurs, a lamp voltage detector 225 detects the voltage-related abnormality, and outputs a lamp voltage error signal 220b to the I/O port 223. The CPU 207 having received the lamp error signal through the I/O port 223 instructs the display controller 206 to display an alarm message, which alarms a user of the fact that current supplied to the lamp or voltage applied thereto is abnormal, on the monitor 216. Since occurrence of an abnormality is visually notified using the monitor 216, a user immediately becomes aware of the system error and can take prompt action to replace the lamp with a new one.

Incidentally, the means for alarming a user of the fact that the current-related or voltage-related abnormality has occurred in the lamp is not limited to displaying of a message on the monitor 216. Alternatively, the alarming means may be visual alarming to be performed using an alarming LED included in the operation panel, acoustic alarming to be performed using an acoustic alarming means such as a buzzer, or a combination of these means.

Figure 15:
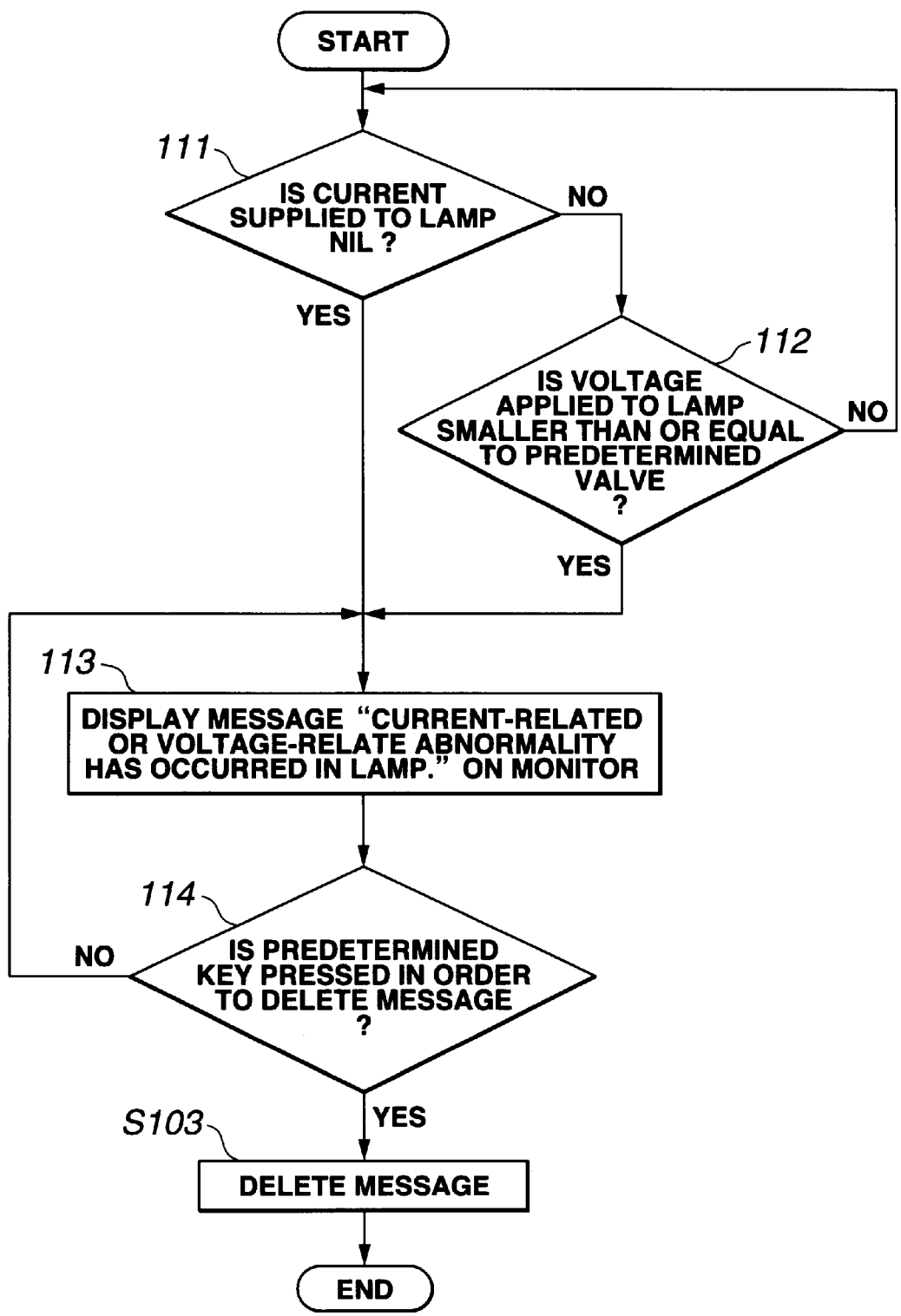
FIG. 15 is a flowchart describing processing to be performed by a CPU when current or voltage supplied or applied to the lamp is abnormal.

FIG. 15 is a flowchart describing processing to be performed by the CPU when a current-related or voltage-related abnormality occurs.

After the power supply is turned on, the lamp current detector 226 outputs a low-level signal as the lamp current error signal 220c through the I/O port 223. The lamp voltage detector 225 outputs a low-level signal as the lamp voltage error signal 220b through the I/O port 223. This is because both the lamp current error signal 220c and lamp voltage error signal 220b are active high. Immediately after the power supply is turned on, the lamp current signal 220c and lamp voltage error signal 220b are driven low in order to reset detection of the current-related or voltage-related abnormality of the lamp. After both the lamp current error signal 220c and lamp voltage error signal 220b are driven low, the lamp current detector 226 and lamp voltage detector 225 start detecting current and voltage supplied or applied to the lamp. If it is detected that the current supplied to the lamp is nil (current-related abnormality), a high-level signal is outputted as the lamp current error signal 220c through the I/O port 223. The high-level signal is transmitted to the CPU 207. Since the high-level signal is transmitted, the CPU 207 judges that the current supplied to the lamp is nil. This means that a judgment is made affirmatively at step S111. If a judgment is made affirmatively at step S111, a control signal is outputted to the display controller 206 so that a message "A current-related/voltage-related abnormality has occurred in the lamp." (or "A current-related abnormality has occurred in the lamp.") will be displayed on the monitor 216 (S113).

Even when it is judged at step S111 that the current supplied to the lamp is normal, if voltage applied to the lamp is equal to or smaller than a predetermined value (voltage-related abnormality), a high-level signal is outputted as the lamp voltage error signal 220b through the I/O port 223. In response to the lamp voltage error signal 220b, the CPU 207 outputs a control signal to the display controller 206 so that a message "A current-related/voltage-related abnormality has occurred in the lamp." (or "A voltage-related abnormality has occurred in the lamp.") will be displayed on the monitor 216 (S113).

If the error message "A current-related/voltage-related abnormality has occurred in the lamp." is displayed at step S113, as long as a user wants to proceed with examination, the user must immediately turn off the power supply and replace the lamp with a new one. If the user wants to delete the error message displayed on the monitor 216 before turning off the power supply, the user presses a predetermined key (for example, an Esc key) included in the keyboard 215. The CPU 207 judges whether the predetermined key is pressed in order to delete the message (S114). If the predetermined key is not pressed and the power supply is not turned off, a judgment is made negatively at step S114. The error message remains displayed on the monitor 216. If the predetermined key is pressed, a judgment is made affirmatively at step S114. The error message displayed on the monitor 216 is deleted.

If the current supplied to the lamp is detected to be normal and the voltage applied thereto is detected to be equal to or larger than the predetermined value, that is, if no abnormality has occurred in the lamp 227, low-level signals are outputted as the lamp current error signal 220c and lamp voltage error signal 220b through the I/O port 223. Moreover, current or voltage supplied or applied to the lamp is detected again (the result of detection is fed back in order to make a judgment at step S202). If no abnormality has occurred in the lamp 27, detection of current or voltage supplied or applied to the lamp is continuously performed.

Next, a third embodiment will be described below.

Figure 16:
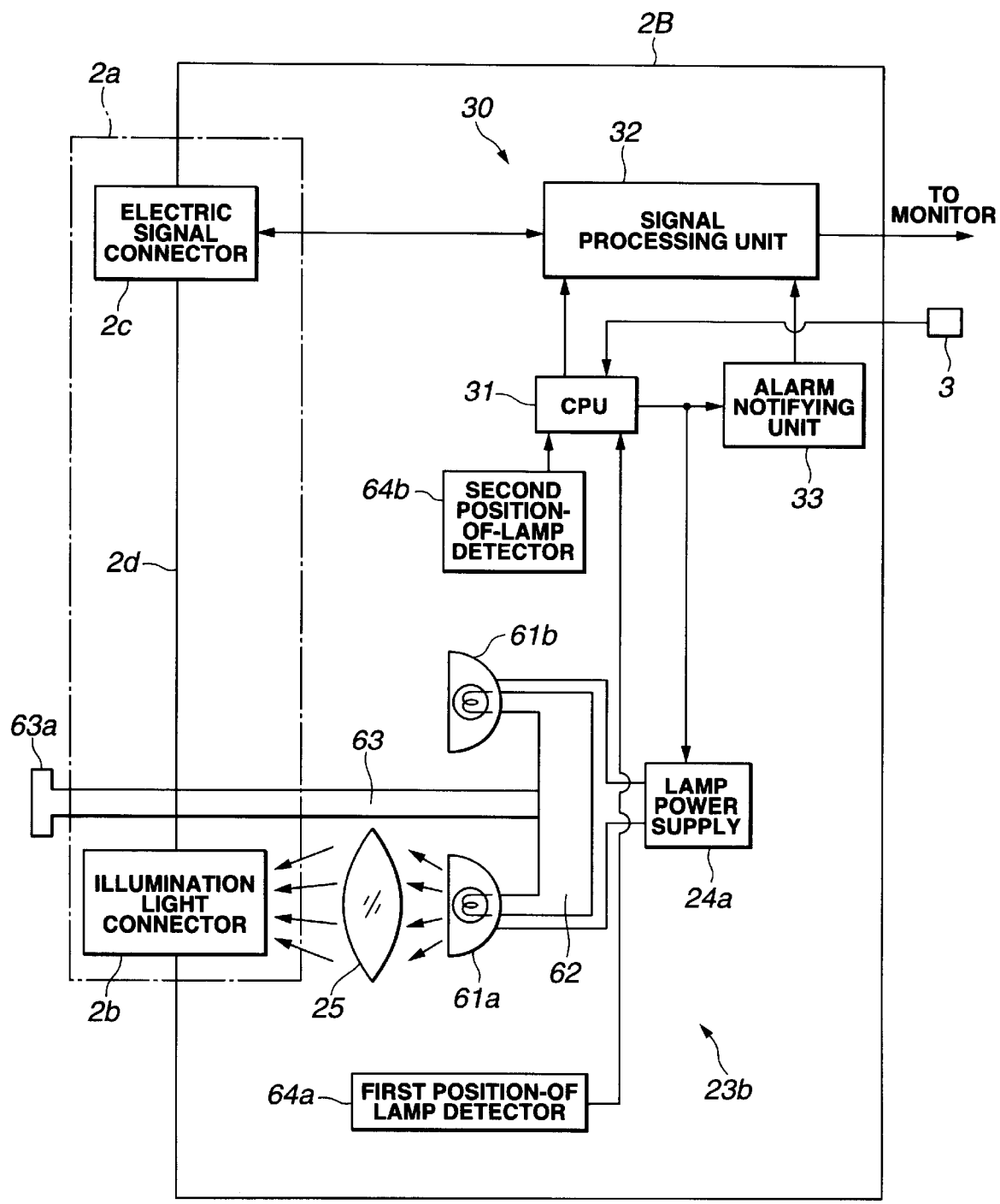
FIG. 16 is an explanatory block diagram showing the configuration of a main apparatus of an endoscope system in accordance with a third embodiment of the present invention.
Figure 17:
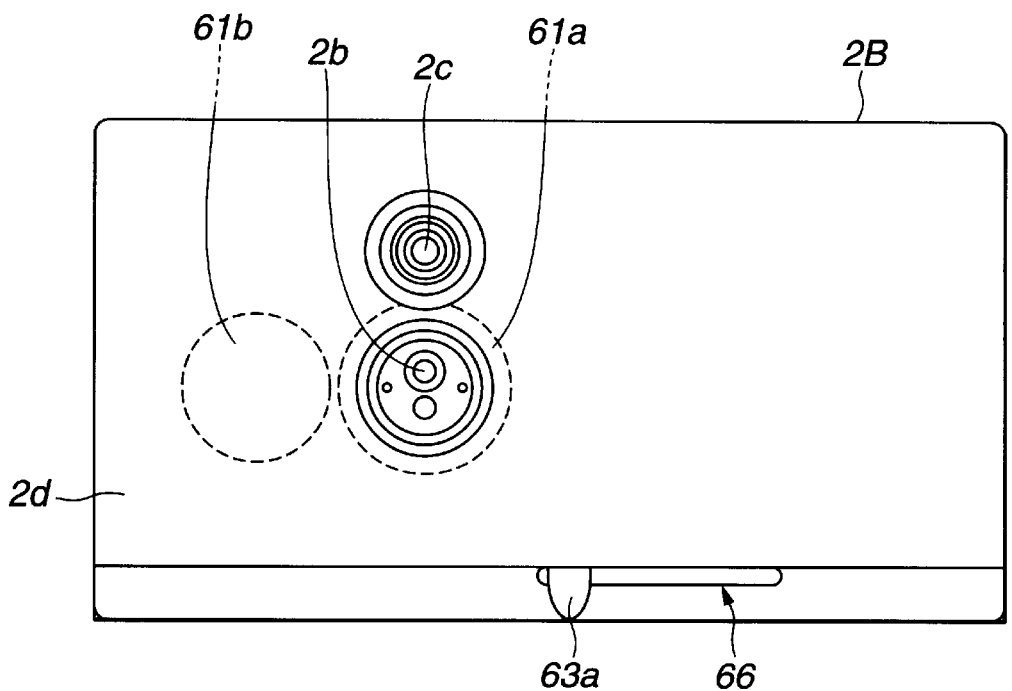
FIG. 17 is an explanatory diagram showing the use of a first lamp as an illuminating lamp.
Figure 18:
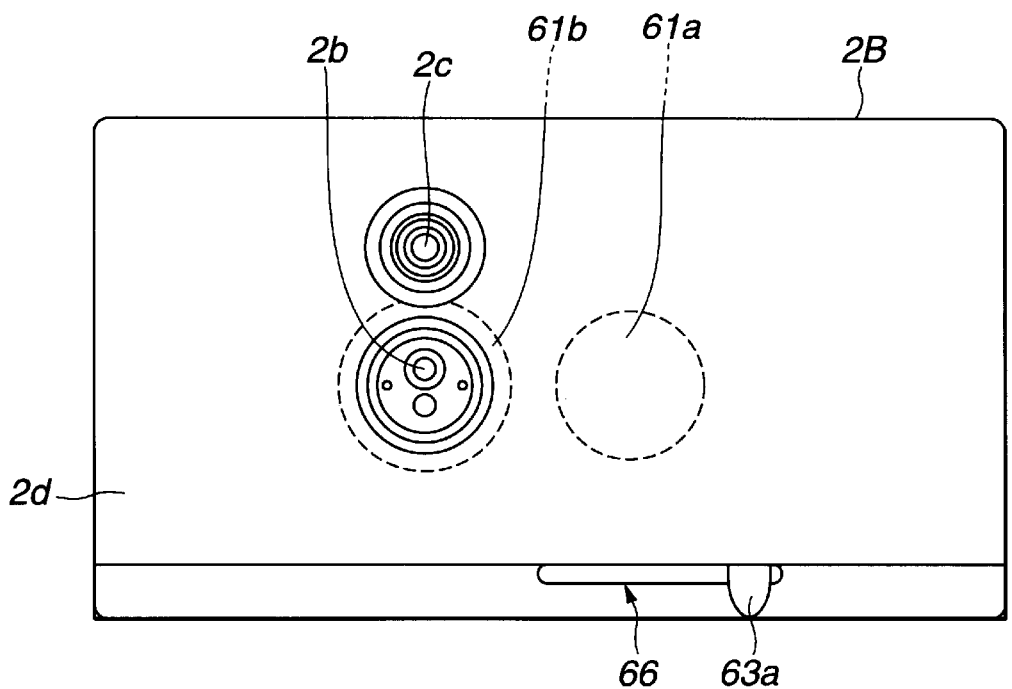
FIG. 18 is an explanatory diagram showing the use of a second lamp as an illuminating lamp.

FIG. 16 to FIG. 18 are explanatory diagrams showing the third embodiment of the present invention. FIG. 16 is an explanatory block diagram showing the configuration of a main apparatus having two lamps. FIG. 17 is an explanatory diagram showing the use of a first lamp as an illumination lamp. FIG. 18 is an explanatory diagram showing the use of a second lamp as the illumination lamp.

As shown in FIG. 16, two lamps for supplying illumination light are included in a light source unit 23b incorporated in a main apparatus 2B of an endoscope system in accordance with the present embodiment. When one of the lamps is used for observation, if the lamp becomes unusable during observation, the lamp is changed to the other lamp in order to proceed with observation.

The light source unit 23b incorporated in the main apparatus 2B comprises two lamps 61a and 61b, a lamp holder 62, a lever 63, a first position-of-lamp detector 64a, which is a condition detecting means, placed near the lamp 61a, a second position-of-lamp detector 64b, which is the condition detecting means, placed near the lamp 61b, and a lamp power supply 24a. The lamp holder 62 is a lamp holding member formed so that the lamps 61a and 61b can be moved in predetermined directions within the main apparatus. The lever 63 has one end thereof fixed to the lamp holder 62 and has the other end portion thereof, which is formed as a grip 63a, exposed on a front panel 2d. The grip 63a is moved to slide the lever 63, whereby the lamp 61a or lamp 61b is located on the path of illumination light. The first position-of-lamp detector 64a is a position-of-lamp detecting means that when the lamp 61a is located at a predetermined position on the path of illumination light, outputs a sense signal to the CPU 31. The lamp power supply 24a supplies power selectively to the lamp 61a and lamp 61b in response to a control signal sent from the CPU 31 that has received the sense signal from the position-of-lamp detector 64a or 64b.

The first position-of-lamp detector 64a and second position-of-lamp detector 64b activates a selector switch (not shown) included therein in the same manner as the temperature detector 27 and power detector 51 do, and outputs a sense signal to the CPU 31.

The CPU 31 receives a sense signal from the first position-of-lamp detector 64a or second position-of-lamp detector 64b. When the CPU 31 receives the sense signal from the first position-of-lamp detector 64a, the CPU 31 outputs a control signal, which prompts the lamp power supply 24a to supply power to the lamp 61a, to the lamp power supply 24a. When the CPU 31 receives the sense signal from the second position-of-lamp detector 64b, the CPU 31 outputs a control signal, which prompts the lamp power supply 24a to supply power to the lamp 61b, to the lamp power supply 24a. When the CPU 31 receives no sense signal from the first position-of-lamp detector 64a or second position-of-lamp detector 64b, neither the lamp 61a nor lamp 61b is located at the predetermined position on the path of illumination light. In this case, the CPU 31 outputs a control signal, which prompts the alarm notifying unit 33 to display a message saying that neither of the lamps is placed at the predetermined position, to the alarm notifying unit 33.

Logical actions to be performed by the foregoing lamps and position-of-lamp detectors will be described below.

When the first position-of-lamp detector 64a enters a sense-signal transmitting state and the second position-of-lamp detector 64b enters a no-sense signal transmitting state, the lamp 61a is lit. In contrast, when the first position-of-lamp detector 64a enters the no-sense signal transmitting state and the second position-of-lamp detector 64b enters the sense-signal transmitting state, the lamp 61b is lit. When both the first position-of-lamp detector 64a and second position-of-lamp detector 64b enter the no-sense signal transmitting state, the lamp 61a and lamp 61b are held unlit. At this time, since neither of the lamps is located at the predetermined position, the CPU 31 outputs a control signal that prompts the alarm notifying unit 33 to notify occurrence of an abnormality.

When both the first position-of-lamp detector 64a and second position-of-lamp detector 64b enter the sense-signal transmitting state, the CPU 31 outputs a control signal that prompts the alarm notifying unit 33 to notify occurrence of an abnormality.

As shown in FIG. 16 and FIG. 17, when the lamp 61a is located at the predetermined position on the path of illumination light and lit, the other lamp 61b stands by at a position off the path of illumination light. At this time, the grip 63a of the lever 63 exposed in a lever movement groove 66 formed in the lower part of the front panel 2d of the main apparatus 2B is located at the left-hand end of the lever movement groove 66. Thus, the lamp holder is moved by manipulating the lever 63, whereby one of the plurality of lamps included in the endoscope system is selected and located on the path of illumination light. At this time, the other unselected lamp is located at a standby position off the path of illumination light.

When the lamp 61b is located on the path of illumination light and lit, the grip 63a of the lever 63 is, as shown in FIG. 18, positioned at the right-hand end of the lever movement groove 66. At this time, the first position-of-lamp detector 64a enters the no-sense signal transmitting state and the second position-of-lamp detector 64b enters the sense-signal transmitting state. Consequently, the lamp 61b is lit.

The other components are identical to those of the first and second embodiments. The same reference numerals will be assigned to the identical components, and the description of the components will be omitted.

Operations to be exerted by the main apparatus 2B having the foregoing components will be described below.

First, the grip 63a of the lever 63 that is exposed on the front panel 2d is, as shown in FIG. 17, positioned at the left-hand end of the lever movement groove 66. At this time, the first position-of-lamp detector 64a enters the sense-signal transmitting state and the second position-of-lamp detector 64b enters the no-sense signal transmitting state. Consequently, the CPU 31 instructs the lamp power supply 24a to supply power only to the lamp 61a. Therefore, the lamp 61a is lit. Light emitted from the lamp 61a is passed through the condenser 25, propagated over the light guide 21, and radiated forwards from the distal structure 14.

During endoscopic examination, the lamp 61a may burn out because the service life thereof has completed its span. In this case, the grip 63a of the lever 63 that is exposed on the front panel 2d is, as shown in FIG. 18, moved rightwards within the lever movement groove 66. This causes the lamp holder 62 to slide in the same direction. Consequently, the lamp 61a moves off the path of illumination light, and the lamp 61b that is on standby enters the path of illumination path.

At this time, the first position-of-lamp detector 64a enters the no-sense signal transmitting state and the second position-of-lamp detector 64b enters the sense-signal transmitting state. Consequently, the CPU 31 outputs a control signal to the lamp power supply 24a, and thus instructs the lamp power supply 24a to supply power to the lamp 61b instead of the lamp 61a. Thus, the lamp 61b is lit and observation can be continuously performed using the endoscope.

While the grip 63a of the lever 63 is being moved, if the movement to be performed for switching the lamps is suspended, neither the lamp 61a nor the lamp 61b is located on the path of illumination light. In other words, the first position-of-lamp detector 64a and second position-of-lamp detector 64b enter the no-sense signal transmitting state. The CPU 31 therefore outputs a control signal, which prompts the alarm notifying unit 33 to notify occurrence of an abnormality, to the alarm notifying unit 33. Besides, the lamp power supply 24a stops supplying power to the lamp 61a or 61b. At this time, a predetermined message informing an operator or the like of the fact that the lamp is put out because the position of the lamp is abnormal is, as shown in FIG. 7, displayed in the message display field 41 while being superimposed on an endoscopic view image. Moreover, a buzzer may be sounded. In this case, a sound control means is included in the alarm notifying unit 33.

Both the first position-of-lamp detector 64a and second position-of-lamp detector 64b enter the no-sense signal transmitting state during switching of the lamps. Displaying of an alarm message or sounding of a buzzer should be disabled during switching of lamps. For this purpose, when a predetermined time has elapsed since the first position-of-lamp detector 64a and second position-of-lamp detector 64b entered the no-sense signal transmitting state, the CPU 31 outputs a control signal to the alarm notifying unit 33. The predetermined time is long enough for an operator or a person concerned to switch the lamps. Even if the first position-of-lamp detector 64a and second position-of-lamp detector 64b enter the no-sense signal transmitting state, as long as the predetermined time has not elapsed, the message informing the operator of the fact that the lamp is put out because the position of the lamp is abnormal is not displayed in the message display field 41.

As mentioned above, the plurality of lamps is included in case a lamp burns out during endoscopic examination. A user can switch the positions of the lamps. Moreover, the position-of-lamp detectors are included for detecting whether the lamp is located at the predetermined position on the path of illumination light. If the lamp should be put out because it is not located at the predetermined position, an operator is notified of the reason immediately.

The notified operator may slide the lever to adjust the position of the lamp or take any other prompt action to proceed with examination.

Figure 19:
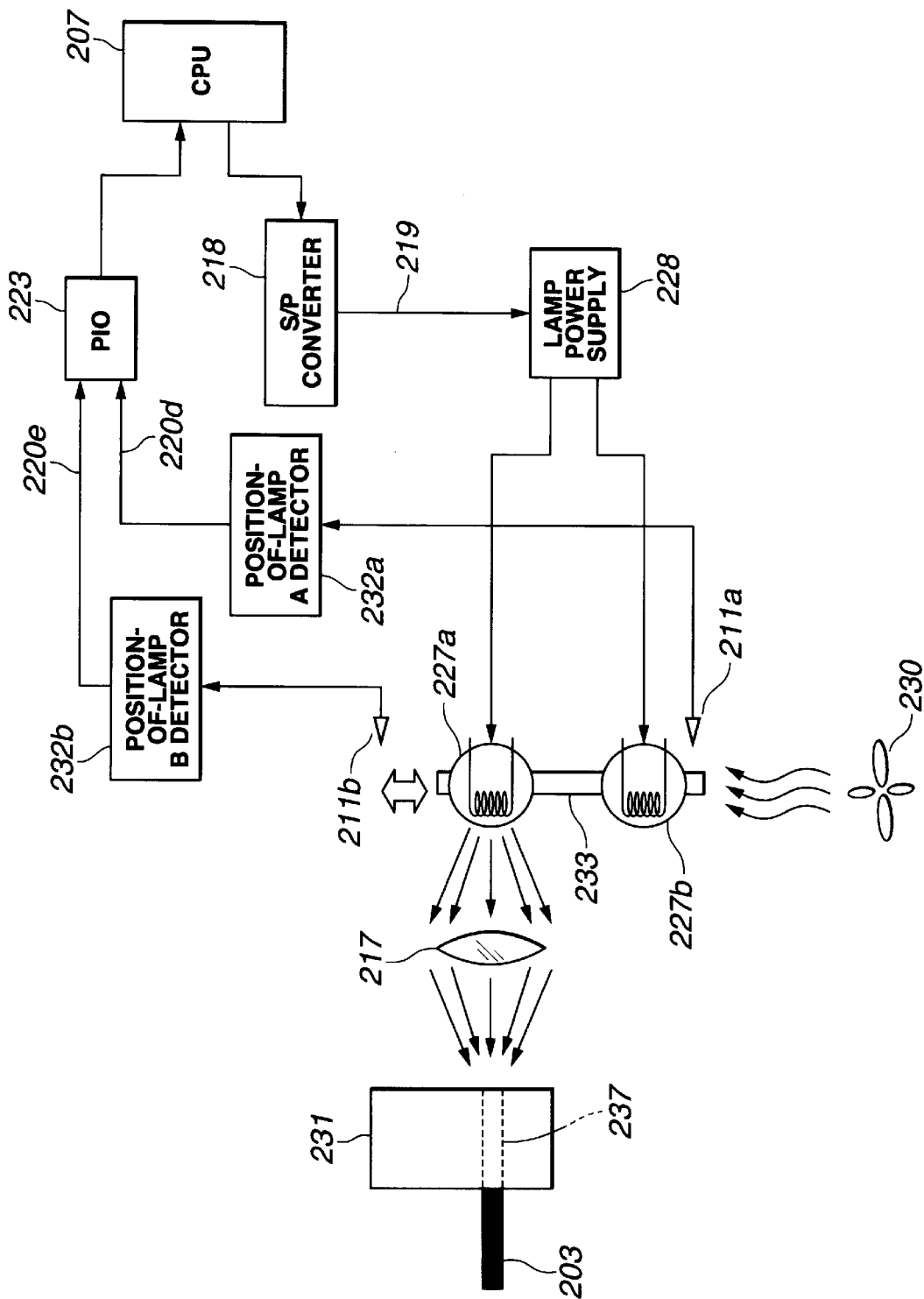
FIG. 19 shows the concrete configuration of a light source unit included in an endoscope system in accordance with a third embodiment.

Next, the light source unit included in the endoscope system in accordance with the third embodiment will be detailed below. FIG. 19 shows the concrete configuration of the light source unit included in the endoscope system in accordance with the third embodiment. The other components are identical to those of the first and second embodiments. The same reference numerals will be assigned to components identical to those shown in FIG. 8 and FIG. 9, and the description of the components will be omitted.

Measures to be taken if the position of a lamp is abnormal will be described in conjunction with FIG. 19. FIG. 19 shows the concrete configuration of the light source unit 210 shown in FIG. 8. The same reference numerals will be assigned to components identical to those of the first and second embodiments, and the description of the components will be omitted.

As described in relation to the second embodiment, a lamp may become unusable because, for example, the filament thereof is fused. An effective solution is inclusion of two lamps (lamp A and lamp B) in an endoscope system. Moreover, a mechanism is included for, if one of the lamps becomes unusable, immediately changing the lamp to the other one.

Figure 20:
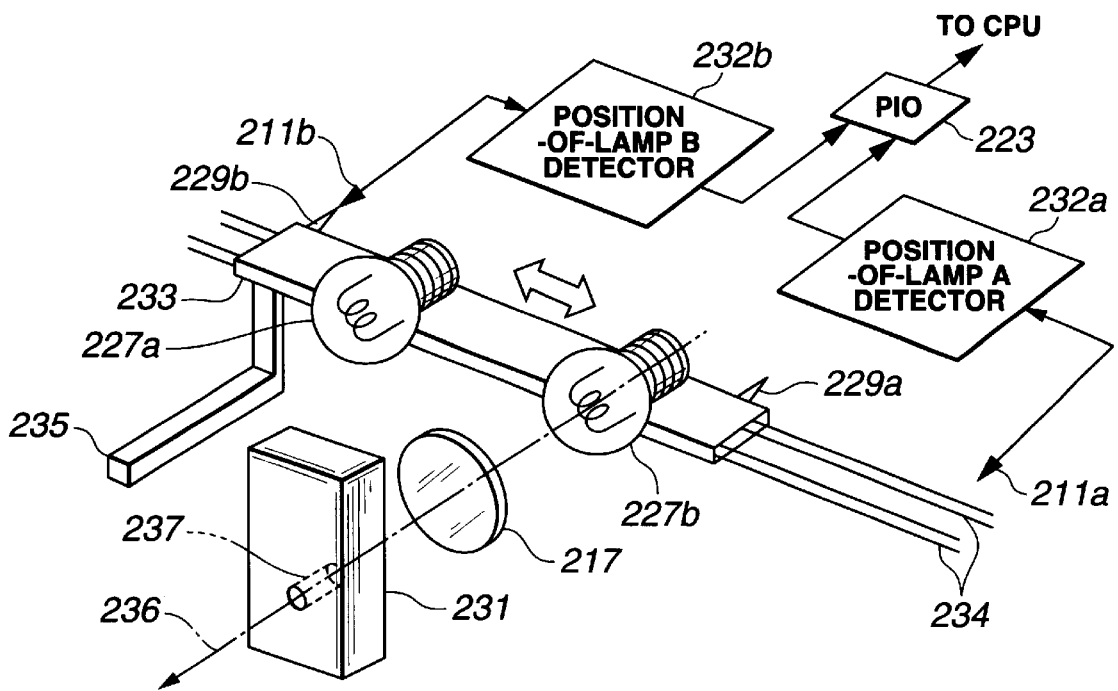
FIG. 20 is an explanatory diagram showing a lamp B located on a light path.
Figure 21:
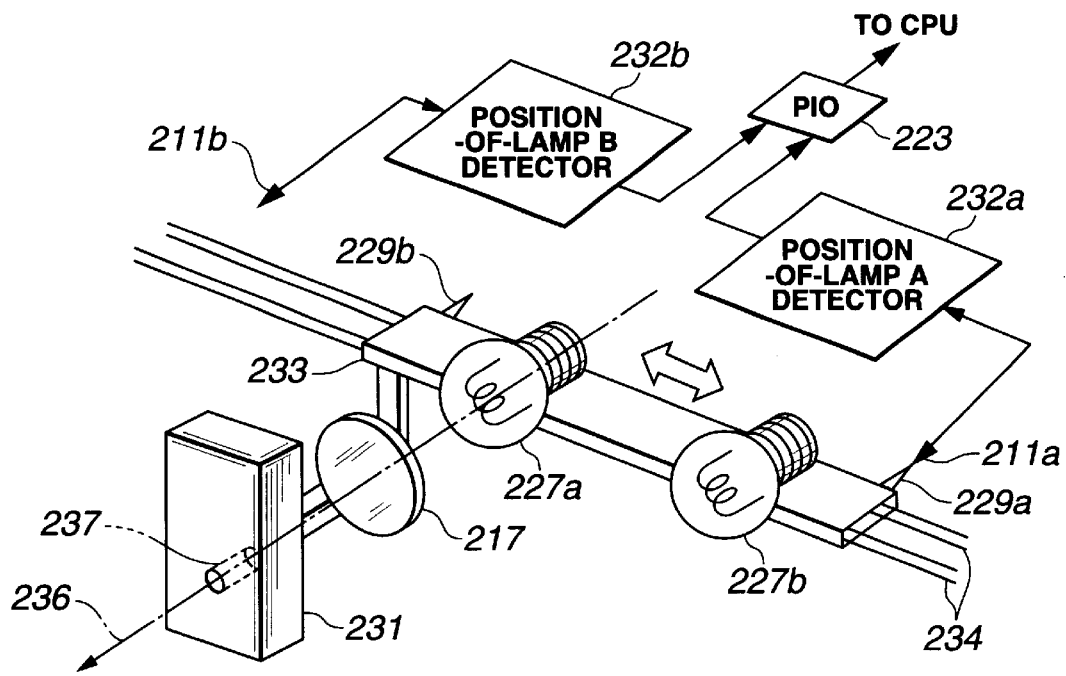
FIG. 21 is an explanatory diagram showing a lamp A located on a light path.

To be more specific, two lamps of lamp A 227a and lamp B 227b are included. A method of controlling lighting of each of the two lamps is identical to the method of controlling the lamp employed in the first embodiment. Namely, the CPU 207 outputs a lighting control signal so as to control lighting of the lamp A 227a and lamp B 227b using the S/P converter 218 and lamp power supply 228. However, the criterion for lighting the lamp 227a or 227b shall be that the lamp 227a or 227b is located on the predetermined light path 236. Referring to FIG. 20 and FIG. 21, a control sequence of controlling lighting of a lamp according to the criterion will be described below. FIG. 20 is an explanatory diagram showing the lamp B 227b located on the light path 236. FIG. 21 is an explanatory diagram showing the lamp A 227a located on the light path 236.

If one of the two lamps becomes unusable, the lamp should be immediately and readily changed to the other one. The lamp A 227a and lamp B 227b are fixed to the lamp holder 233. The lamps 227 and lamp holder 233 each have a mechanism (not shown) that enables easily fixing or unfixing of a lamp. The lamp holder 233 is mounted on sliding rails 234, and can be smoothly slid, on the sliding rails 234, in the only rail direction. A lamp lever 235 is fixed to the lamp holder 233. A user holds the lamp lever 235 to move it laterally. This causes the lamp holder 233 to move laterally on the sliding rails 234. Synchronously with the movement, the lamp A 227a and lamp B 227b fixed to the lamp holder 233 move laterally on the sliding rails 234.

The light path 236 in the endoscope system is an imaginary line linking the center of the condenser 217 and the center of the light path hole 237. The light path 236 is orthogonal to the sliding rails 234. When the center of the lamp A 227a or lamp B 227b coincides with the light path 236, an amount of light emitted from the lamp to the light guide 203 is maximized. In order to produce a clear endoscopic image, the amount of light emitted from a lamp should, preferably, be maximized during observation. Therefore, for observation, the lamp 227 must be located on the light path 236. In contrast, when the lamp 227 lies off the light path 236, the condition is not optimal to observation. Lighting of the lamp 227 should therefore be disabled. Only when the lamp A 227a or lamp B 227b is located on the light path 236, the lamp is lit. Consequently, the present endoscope system can provide a user with an, optimal endoscopic image all the time.

Pairs of position-of-lamp detection terminals and lamp holder terminals are included as a means for enabling the CPU 207 to sense whether a lamp is located on the light path 236. Lamp holder terminals 229a and 229b are fixed to the lamp holder 233. When a user holds the lamp lever 235 to move the lamp holder 233, the lamp holder terminals 229 move. A position-of-lamp A detection terminal 211a is, as shown in FIG. 21, brought into contact with the lamp holder terminal 229a only when the lamp A 227a is located on the light path 236. A position-of-lamp B detection terminal 211b is brought into contact with the lamp holder terminal 229b only when the lamp B 227b is located on the light path 236. The position-of-lamp A detection terminal 211a and position-of-lamp B detection terminal 211b are thus secured in the main apparatus. When the position-of-lamp detection terminal 211 and lamp holder terminal 229 that are paired with each other come into contact with each other, the associated lamp can be lit. However, a movable space in which the lamp holder 233 is movable is limited. Therefore, the lamp holder terminal 229a and position-of-lamp B detection terminal 211b or the lamp holder terminal 229b and position-of-lamp A detection terminal 211a will not come into contact with each other. When the position-of-lamp A detection terminal 211a and lamp holder terminal 229a are not in contact with each other, a position-of-lamp A detector 232a outputs a position-of-lamp A error signal 220d through the I/O port 223. When the position-of-lamp B detection terminal 211b and lamp holder terminal 229b are not in contact with each other, a position-of-lamp B detector 232b outputs a position-of-lamp B error signal 220e through the I/O port 223. The position-of-lamp error signals 220a are outputted to the CPU 207 through the I/O port 223. The CPU 207 selects a lamp whose position is not detected as an error, and instructs lighting of the selected lamp alone.

The concrete relationships between the positions of the lamps and a lighting instruction are listed below.

TABLE

| | States of the position-of-lamp A detection terminal 211a and lamp holder terminal 229a | States of the position-of-lamp B detection terminal 211b and lamp holder terminal 229b | States of lamp |
|---|---|---|---|
| i) | In contact with each other | Not in contact with each other | Lamp A: lit Lamp B: put out |
| ii) | Not in contact with each other | In contact with each other | Lamp A: put out Lamp B: lit |
| iii) | Not in contact with each other | Not in contact with each other | Lamp A: put out Lamp B: put out |

TABLE-continued

| States of the position-of-lamp A detection terminal 211a and lamp holder terminal 229a | States of the position-of-lamp B detection terminal 211b and lamp holder terminal 229b | States of lamp |
| --- | --- | --- |
| iv) In contact with each other | In contact with each other | Unfeasible (logically unthinkable) |

In case of item i), the lamp A 227*a* located on the light path 236 is lit. In case of item ii), the lamp B 227*b* located on the light path 236 is lit. In case of item iii), the two lamps are located off the light path 236 and therefore held unlit. The case of item iii) is a case where the positions of the lamps are abnormal, wherein an amount of light emitted from the lamp and radiated from the distal end of the endoscope 201 is insufficient for observation. The CPU 207 instructs the display controller 206 to display a warning message, which says that the positions of the lamps are abnormal, on the monitor 216. Thus, occurrence of an abnormality is visually notified using the monitor 216. This enables a user to immediately sense a system error and to take prompt action to move the lamps to their right positions.

However, the means for warning that a current-related or voltage-related abnormality has occurred in a lamp is not limited to displaying of a message on the monitor 216. Alternatively, the warning means may be visual warning to be performed using a warning LED included in the operation panel, acoustic warning to be performed using a buzzer, or a combination of these means.

Figure 22:
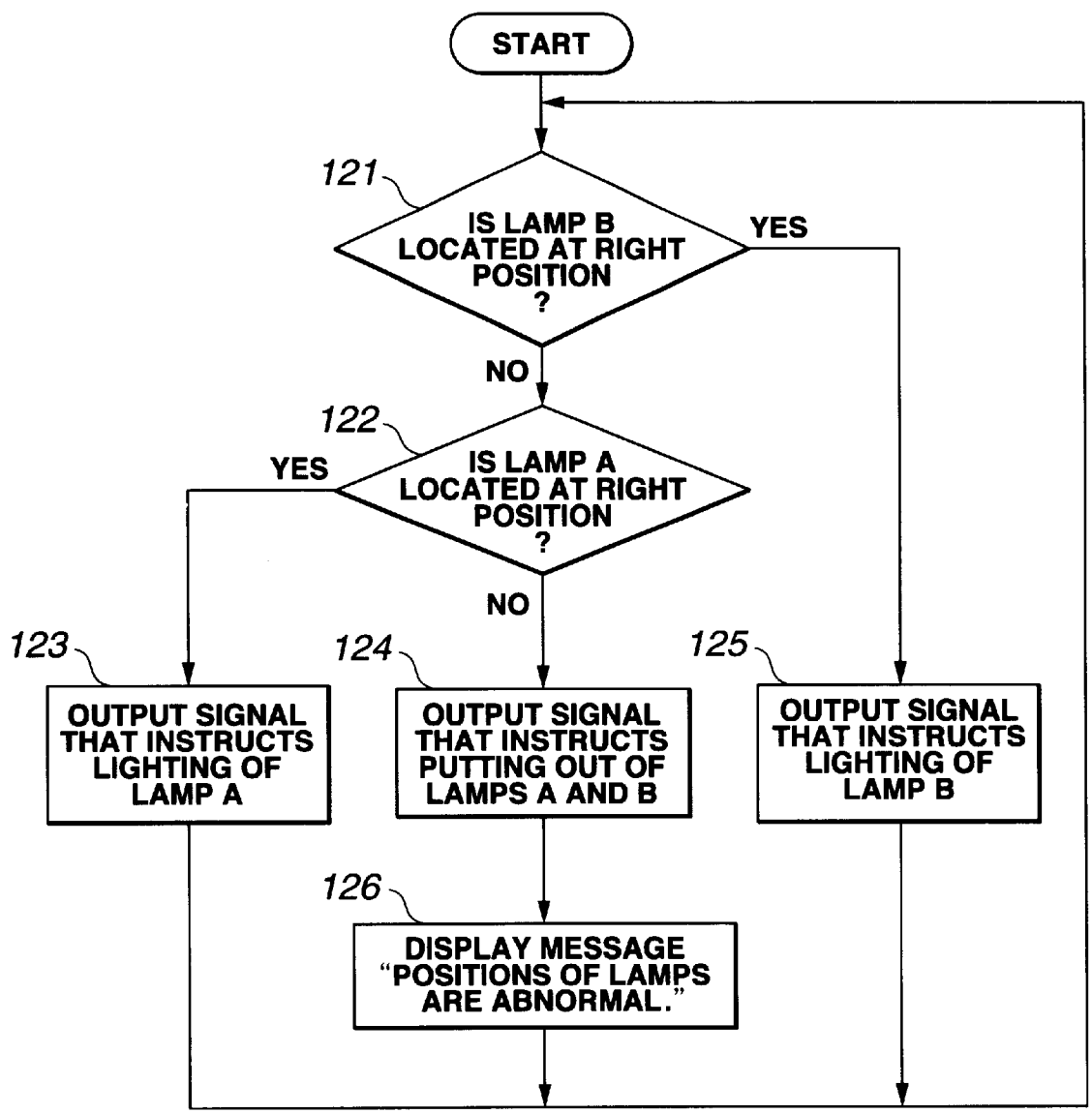
FIG. 22 is a flowchart describing processing to be performed by a CPU when the position of a lamp is abnormal.

FIG. 22 is a flowchart describing processing to be performed by the CPU when the positions of the lamps are abnormal.

After the power supply is turned on, a high-level signal is outputted as the position-of-lamp A error signal 220*d* from the position-of-lamp A detector 232*a* through the I/O port 223. Moreover, a high-level signal is outputted as the position-of-lamp B error signal 220*e* from the position-of-lamp B detector 232*b* through the I/O port 223. Incidentally, these signals are active high. Consequently, the CPU 207 instructs the lamp power supply 228 to put out the two lamps. Specifically, immediately after the power supply is turned on, the positions of the two lamps A and B are considered to be abnormal. Immediately after the main apparatus is activated, the two lamps are held unlit.

Thereafter, the position-of-lamp B detector 232*b* detects the position of the lamp B. When the lamp B is located on the light path 236, a high-level signal is developed at the position-of-lamp B detection terminal 211*b* and outputted to the position-of-lamp B detector 232*b*. At this time, a low-level signal is outputted as the position-of-lamp B error signal 220*e* from the position-of-lamp B detector 232*b* through the I/O port 223. At this time, it is unfeasible that the lamp A is located on the light path 236. A high-level signal is therefore outputted as the position-of-lamp A error signal 220*d* from the position-of-lamp A detector 232*a* through the I/O port 223.

The CCU 207 judges from the aforesaid table and the information received through the I/O port 223 whether the lamp B is located at the right position. In the foregoing case, the CPU 207 judges that the lamp B is located at the right position. A judgment is made affirmatively at step S121. The CPU 207 outputs a serial signal, which prompts lighting of a lamp, to the S/P converter 218 (S125). The S/P converter 218 converts the serial signal into a parallel signal. A lamp B lighting instruction signal is then outputted to the lamp power supply 228. Consequently, the lamp B is lit.

If it is judged at step S121 that the lamp B is not located on the light path 236, a low-level signal is developed at the position-of-lamp B detection terminal 211*b* and outputted to the position-of-lamp B detector 232*b*. At this time, the position-of-lamp B detector 232*b* outputs a high-level signal as the position-of-lamp B error signal 220*e* through the I/O port 232.

Furthermore, when the lamp A is located on the light path 236, a high-level signal is developed at the position-of-lamp A detection terminal 211*a* and outputted to the position-of-lamp A detector 232*a*. The position-of-lamp A detector 232*a* then outputs a low-level signal as the position-of-lamp A error signal 220*d* through the I/O port 223.

The CPU 207 judges from the aforesaid table and the information received through the I/O port 223 whether the lamp A is located at the right position. In the foregoing case, the CPU 207 judges that the lamp A is located at the right position. Therefore, a judgment is made affirmatively at step S122. A serial signal that prompts lighting of the lamp A is then outputted to the S/P converter 18 (S123). Consequently, the lamp A is lit.

If it is judged at step S122 that the lamp A is not located on the light path 236, a low-level signal is developed at the position-of-lamp A detection terminal 211*a* and outputted to the position-of-lamp A detector 232*a*. The position-of-lamp A detector 232*a* then outputs a high-level signal as the position-of-lamp A error signal 220*d* through the I/O port 223. In this case, both the lamps A and B are located off the light path 236. The CPU 207 having received the information through the I/O port 223 outputs a serial signal, which prompts putting out of the lamps A and B, to the S/P converter 218 (S124). The S/P converter 218 converts the serial signal into a parallel signal. Consequently, a putting-out instruction is outputted to the lamp power supply 228 relative to both the lamps A and B. The two lamps are therefore not lit. The CPU 207 instructs the display controller 206 to display a warning message, which says that the positions of the lamps are abnormal, on the monitor 216 (S126).

After the lamp A is lit, the lamp B is lit, or the message saying that the positions of the lamps are abnormal is displayed, the positions of the lamps are detected again (control is returned to step S121). The positions of the lamps are therefore continuously detected all the time.

Figure 23:
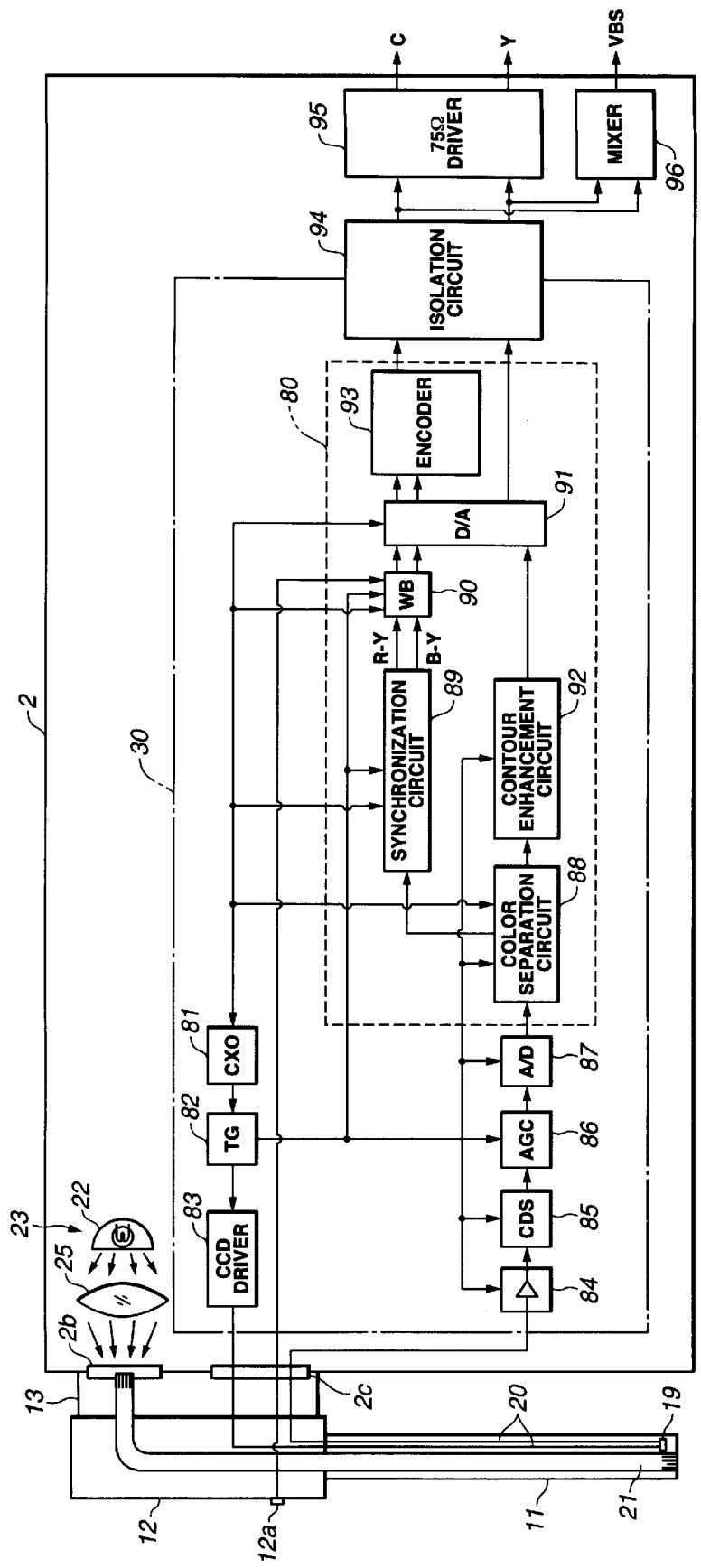
FIG. 23 is an explanatory block diagram showing the outline configuration of an electronic endoscope system.

In the electronic endoscope system, an isolation circuit must be interposed between a patient circuit and a secondary circuit in order to enable transfer of signals therebetween. When the electronic endoscope system includes a digital signal processor (DSP), what kind of application circuit should be adopted is predefined. If the patient circuit and secondary circuit are separated from each other with the application circuit therebetween, many signals must be transferred. This poses a problem in that the larger the number of transferred signals is, the larger the isolation circuit gets in scale. There is therefore an increasing demand for a compact isolation circuit. In the aforesaid embodiments, as shown in FIG. 23, a video signal is transmitted to the secondary circuit with a luminance signal Y and a color signal C thereof separated from each other. FIG. 23 is an explanatory block diagram showing the outline configuration of an electronic endoscope system.

Specifically, an electronic endoscope system comprises, as shown in FIG. 23, an endoscope 1, a processor 30, and a main apparatus 2. The processor 30 converts an image signal, which is transmitted from a CCD 19 incorporated in the endoscope 1, into a video signal, and displays a view image and various data items on a monitor (not shown). The main apparatus 2 has a light source unit 23, which includes a lamp that supplies illumination light to the endoscope 1, as an integral part thereof.

An operation unit 12 of the endoscope 1 has a white balance control switch (WB) 12a that is used to inform a control value based on which the processor 30 performs white balance control on a video signal.

The processor 30 that is a patient circuit incorporated in the main apparatus 2 includes a crystal oscillator (CXO) 81 that generates a reference clock pulse. The reference clock pulse (reference CK signal) generated by the crystal oscillator 81 is transmitted to each of a timing generator (TG) 82 included in the patient circuit and a video signal processing digital signal processor (hereinafter DSP) 80. The video signal processing DSP 80 has the ability to generate a video signal conformable to a display format adopted for the monitor.

The timing generator 82 generates a CCD driving signal according to the reference clock pulse. A CCD driver 83 drives the CCD 19 according to the timing of the CCD driving signal. The CCD 19 driven according to the timing generates an output signal that represents an object. The CCD 19 has a complementary colors filter that yields an achromatic mixture of cyan, yellow, magenta, or green.

Charge accumulated on the light receiving surface of the CCD 19 is read by scanning the CCD 19 along two lines, to which a driving signal outputted from the CCD driver 83 is applied, at a time according to interlaced scanning. The resultant signal proportional to the read charge is transmitted to the processor 30 over a signal cable 20.

The transmitted image signal is amplified by a predetermined gain by a preamplifier 84 in order to compensate for a loss produced while being transmitted over the signal cable 20. A correlative double sampling (CDS) circuit 85 samples a video signal component from the image signal, and outputs the component as a video signal to an automatic gain control (AGC) circuit 86.

The video signal transferred to the AGC circuit 86 has the level thereof adjusted through gain control, and is then outputted to an A/D converter 87. The A/D converter 87 digitizes the video signal and outputs the resultant signal to a color separation circuit 88 included in the video signal processing DSP 80.

The color separation circuit 88 converts the received video signal into a luminance signal Y and chrominance signals R-Y and B-Y. The chrominance signals separated by the color separation circuit 88 are line-sequentially transferred. In other words, the chrominance signals R-Y and B-Y are alternately transferred line by line, that is, line-sequentially. The line-sequentially transferred chrominance signals are received by a synchronization circuit 89.

The chrominance signals R-Y and B-Y received by the synchronization circuit 89 are synchronized while being transferred to destinations that are alternated line by line according to the reference clock pulse sent from the timing generator 82. Consequently, the chrominance signals are outputted as synchronized chrominance signals to a white balance (WB) control circuit 90.

The white balance control circuit 90 controls a balance of white and red or blue represented by either of the synchronized chrominance signals. More particularly, when the white balance switch 12a is pressed with a white object imaged, the white balance control circuit 90 controls a gain to be given to each of the synchronized chrominance signals so that the chrominance signals R-Y and B-Y will assume that same level. Consequently, the chrominance signals whose levels are equalized are outputted to a D/A converter 91.

On the other hand, the luminance signal separated by the color separation circuit 88 is passed through a contour enhancement unit 92 and outputted to the D/A converter 91.

The luminance signal and line-sequential chrominance signals R-Y and B-Y that are received by the D/A converter 91 are converted from a digital form into an analog form. The line-sequential chrominance signals R-Y and B-Y that are digitized are outputted to an encoder 93, and the digitized luminance signal is outputted to an isolation circuit 94.

The encoder 93 performs quadrature modulation on the line-sequential chrominance signals R-Y and B-Y, and outputs a resultant signal as a color signal C to the isolation circuit 94 that can transmit a high-frequency analog signal.

Consequently, the isolation circuit 94 receives the analog luminance signal Y and color signal C. The analog luminance signal Y and color signal C are transferred from the isolation circuit to the secondary circuit.

The luminance signal and color signal transferred to the secondary circuit are received by a 75-ohm driver 95 and a mixer 96 respectively. The mixer 96 synthesizes the luminance signal and color signal so as to generate a composite video signal (VBS). The mixer 96 includes a 75-ohm driver. Therefore, the composite video signal VBS is outputted to the monitor as it is.

Thereafter, the composite video signal VBS and a Y/C-separated video signal are applied to a connector (not shown) via which the main apparatus is connected to an external apparatus, and thus outputted from the main apparatus 2.

As mentioned above, the line-sequential chrominance signals R-Y and B-Y are modulated within the patient circuit and thus converted into the color signal C. The isolation circuit transmits the analog luminance signal and color signal to the secondary circuit. This results in a decreased number of transmission lines. The other components are identical to those of the aforesaid embodiments. The same reference numerals will be assigned to components identical to those of the aforesaid embodiments, and the description of the components will be omitted.

In the electronic endoscope system, not only an endoscope image but also patient data is displayed on the screen of a monitor. The monitor is used to enter the patient data at a keyboard or any other input unit. Therefore, the monitor included in the electronic endoscope system is demanded to be easy to see. Moreover, the monitor is demanded to be easy to manipulate and user-friendly.

Figure 24:
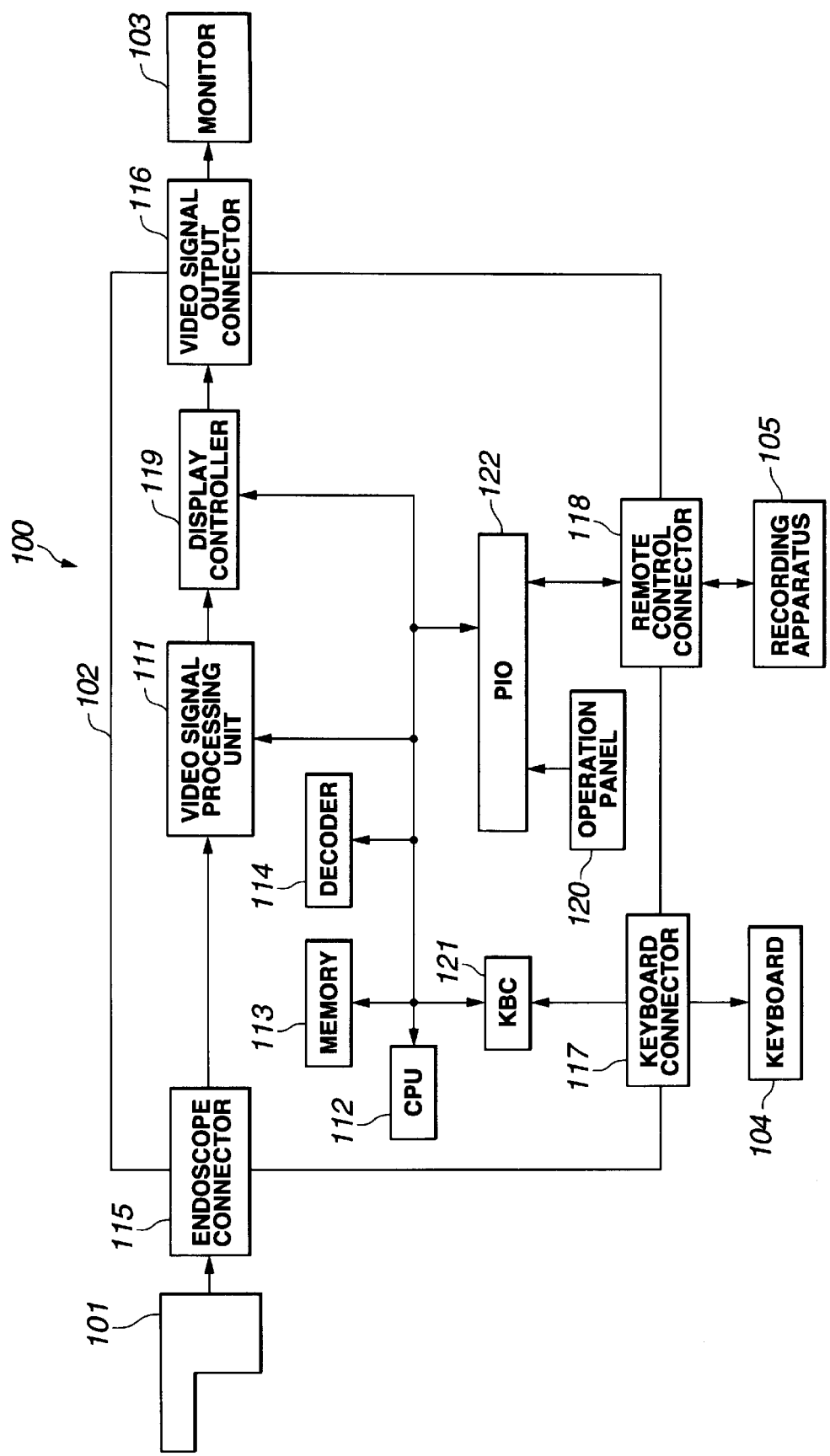
FIG. 24 is an explanatory diagram showing the configuration of an electronic endoscope system.

FIG. 24 is an explanatory diagram showing the configuration of an electronic endoscope system. As shown in FIG. 24, an electronic endoscope system 100 comprises an electronic endoscope 101, a processor 102, a monitor 103, a keyboard 104, and any of various types of recording apparatuses 105. The monitor 103 is connected to the processor 102 and displays an endoscope image. The keyboard 104 is connected to the processor 102 and used to enter various data items and control the system. The recording apparatus 105 records endoscopic image data. The processor 102 controls a CCD (not shown) incorporated in the distal part of the electronic endoscope 101, and includes a circuit that processes an endoscopic image of an object picked up by the CCD so as to generate a predetermined video signal.

The processor 102 includes at least a video signal processing unit 111, a central processing unit (CPU) 112, a memory 113, an address bus and data bus (not shown), a decoder 114, an endoscope connector 115, a video signal output connector 116, a keyboard connector 117, a remote control connector 118, and a display controller 119. The video signal processing unit 111 performs digitization, color correction, contour enhancement, and white balance control on a video signal generated by the electronic endoscope 101. The decoder 114 may be a memory address coder or an I/O address decoder. The endoscope connector 115 serves as any type of input/output port and is used to connect the processor to the electronic endoscope 101. The video signal output connector 116 is used to connect the processor to the monitor 103. The keyboard connector 117 is used to connect the processor to the keyboard 104. The remote control connector 118 is used to connect the processor to the recording apparatus. The display controller 119 renders characters. Furthermore, an operation panel 120 serving as an external input means is formed as part of the front panel of the processor 102. There are also shown a keyboard controller (KBC) 121 and a parallel input/output circuit (PIO) 122.

Figure 25:
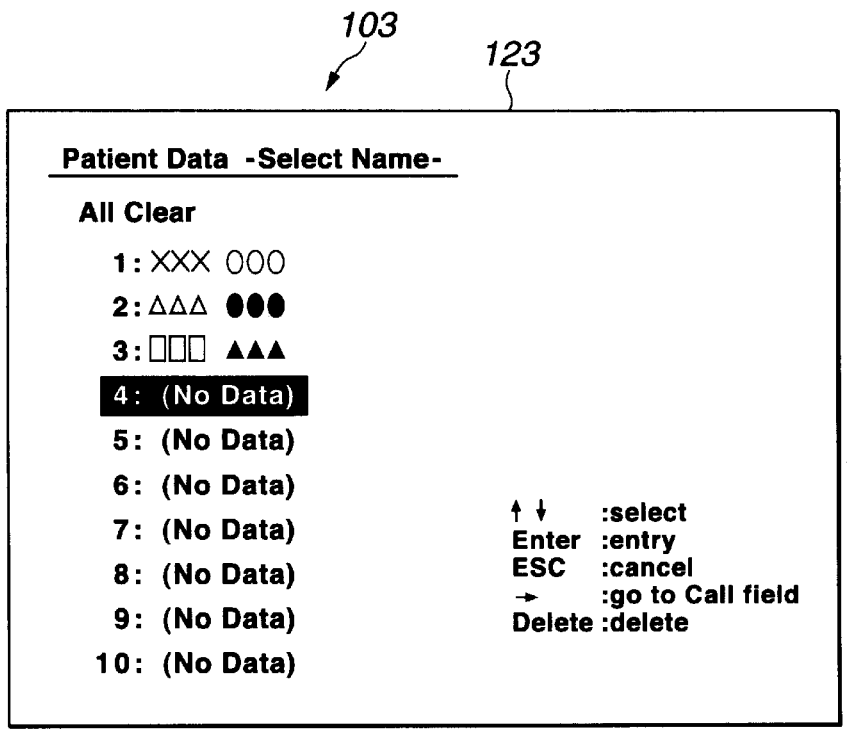
FIG. 25 shows an example of a screen image displayed on the screen of a monitor.
Figure 26:
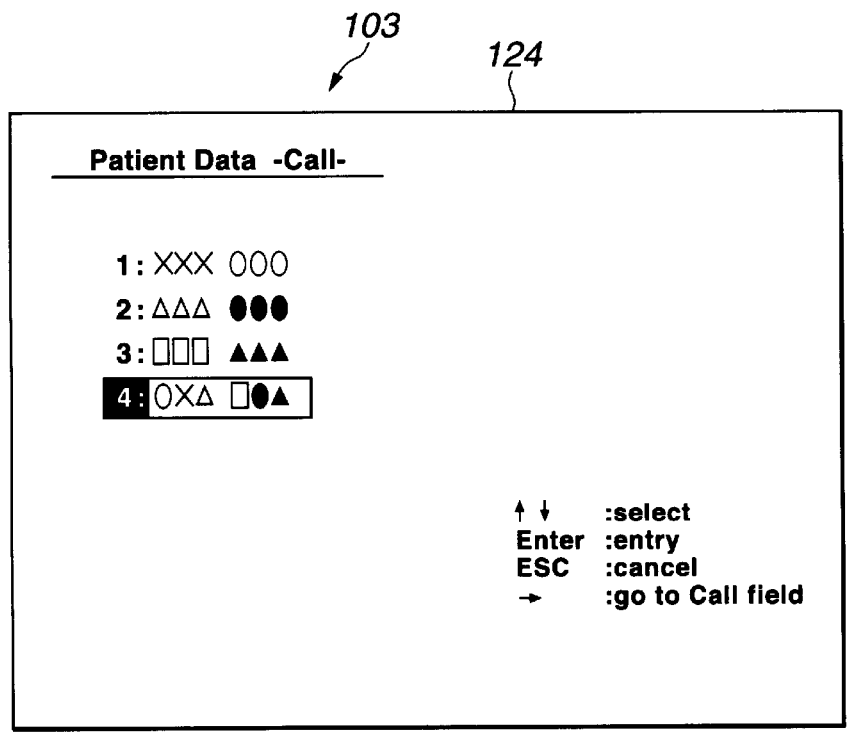
FIG. 26 shows another example of a screen image displayed on the screen of the monitor.

FIG. 25 shows an example of a screen image displayed on the screen of the monitor. As shown in FIG. 25, a screen image used to store patient data or the like in the electronic endoscope system in advance or a so-called registration screen 123 is displayed on the screen of the monitor 103. FIG. 26 shows another example of the screen image displayed on the screen of the monitor. As shown in FIG. 26, a screen image used to retrieve patient data stored using the registration screen 123 or a so-called retrieval screen 124 is displayed on the screen of the monitor 103.

The registration screen 123 and retrieval screen 124 are displayed on the screen of the monitor 103 by performing predetermined manipulations.

Specifically, the registration screen 123 is displayed on the screen of the monitor 103 by selecting a Register key (not shown). The Register key is a predetermined key included in the keyboard 104. The number of persons whose names can be stored in the memory 113 included in the processor 102 after entered at the keyboard 104 is predefined. It is impossible to store a larger number of patient data items than a specified number of patient data items.

When the Register key is pressed, if any patient data is already stored in the memory 113, the stored patient names (specified in item 1 to item 3 in FIG. 25) are displayed as shown in FIG. 25. If the number of patient data items stored in the memory 113 falls below a maximum number of data items that can be stored, characters "No Data" are displayed on the screen in order to indicate that no patient name is specified as an item. When No Data is clicked in the registration screen 123, patient data can be stored in advance by following instructions.

On the other hand, the retrieval screen 124 is displayed on the screen of the monitor 103 by pressing a Retrieve key (not shown). The Retrieve key is one function key included in the keyboard 104. When the Retrieve key is pressed, a list of patient names stored in advance using the registration screen 123 is displayed. When any patient name is selected from the list of patient names, patient data stored in association with the patient name, for example, a name, an ID number, and a date of birth are displayed on the screen of the monitor 103 (not shown).

Moreover, as far as the endoscope system 100 in accordance with the present embodiment is concerned, if a Change key that is a predetermined function key included in the keyboard 104 is pressed with the registration screen 123 displayed, the registration screen is immediately changed to the retrieval screen 124. Namely, if patient data must be retrieved immediately after it is stored using the registration screen 123, the Change key should merely be pressed. With the press of the Change key, the registration screen 123 is changed to the retrieval screen 124. At this time, it is unnecessary to terminate the registration screen 123 and press the Retrieve key. Likewise, when the change key that is a predetermined function key included in the keyboard 104 is pressed with the retrieval screen 124 displayed, the retrieval screen 124 is immediately changed to the registration screen 123.

As mentioned above, the inclusion of the Change key simplifies manipulation of the keyboard and greatly improves the maneuverability.

In the aforesaid embodiment, the Change key is a function key included in the keyboard. However, the Change key is not limited to the function key. Alternately, the Change key may be any other key unused to initiate any arithmetic operation, for example, a cursor or a Tab key, or a combination of keys, for example, a combination of a Ctrl key and a F1 key.

Moreover, screen images interchangeable with a press of the Change key are not limited to the registration screen 123 and retrieval screen 124 but may be any other screen images including a system setting screen that is not shown.

Figure 27:
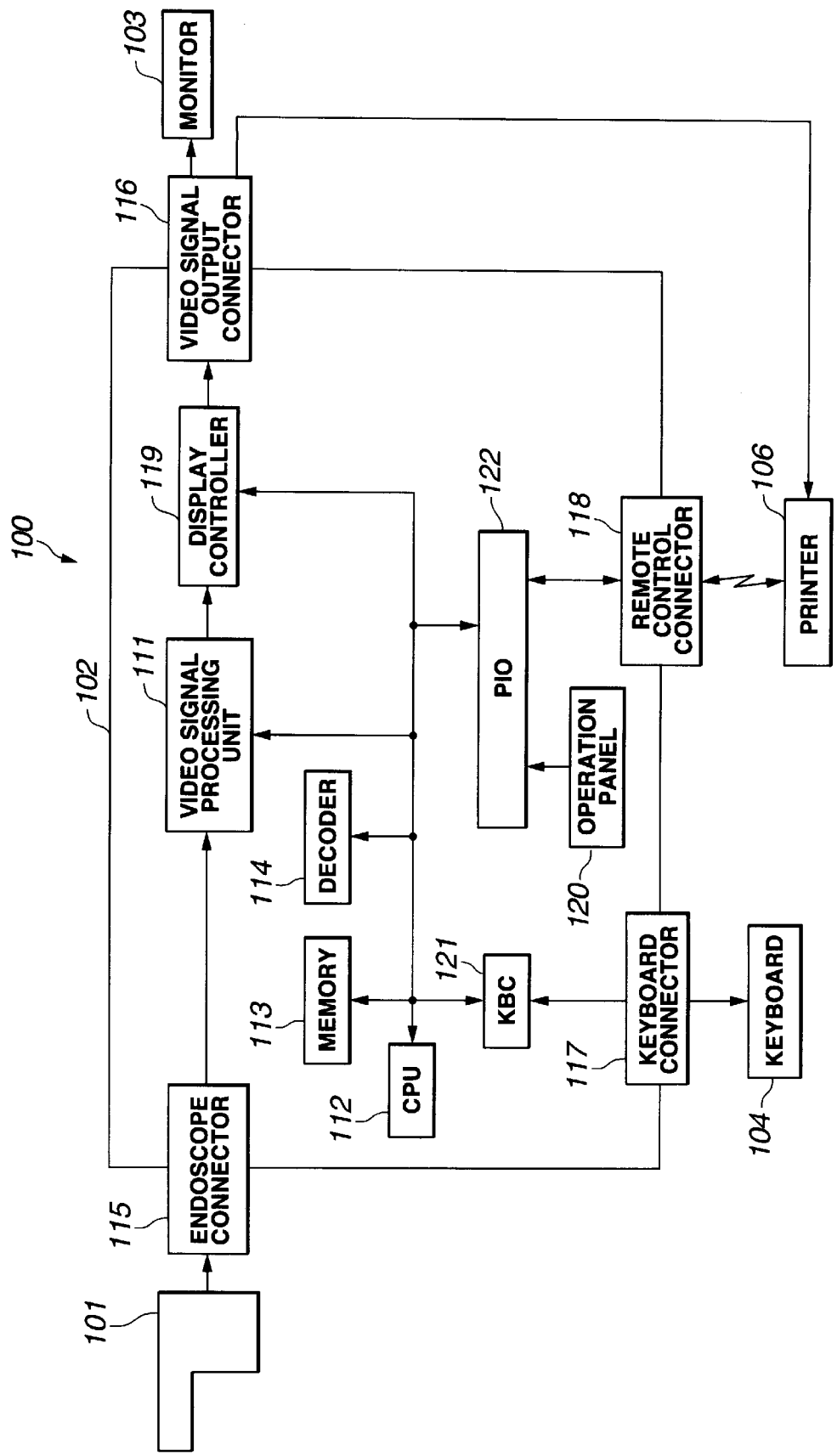
FIG. 27 is an explanatory diagram showing another configuration of an electronic endoscope system.

FIG. 27 is an explanatory diagram showing another configuration of an electronic endoscope system. As shown in FIG. 27, the recording apparatus 105 connected to the processor 102 and used to record endoscopic image data may be, for example, a printer 106. The printer 106 has the ability to print any characters, which a user has arbitrarily entered or designated, on print paper. The user-entered or user-designated characters are printed as a caption that indicates, for example, a hospital name or a comment. Moreover, the caption can be entered using not only the main unit of the printer 106 but also the processor 102 that remotely controls the printer. The other components are identical to those employed in the aforesaid embodiments. The same reference numerals will be assigned to components identical to those of the embodiments, and the description of the components will be omitted.

Figure 28:
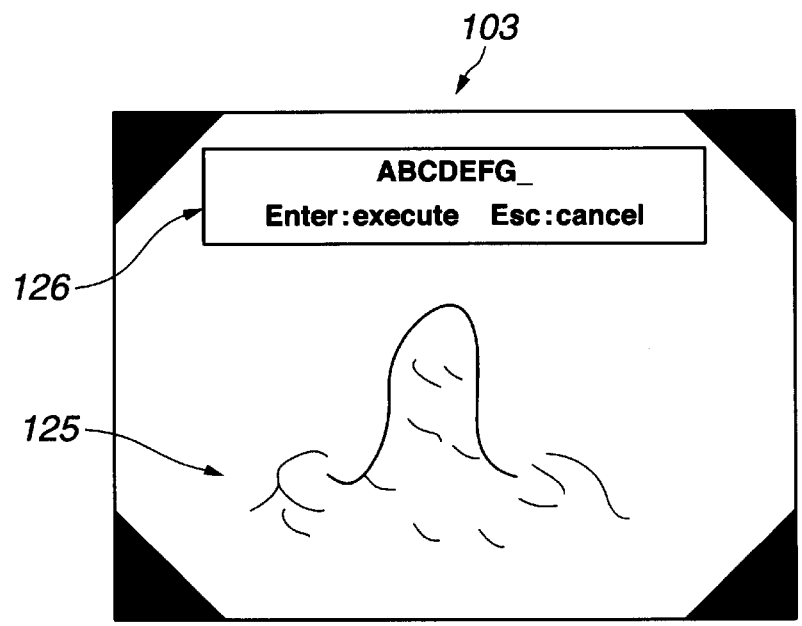
FIG. 28 is an explanatory diagram showing an example of a screen image displayed on the screen of the monitor.

Now, the way of entering a caption by remotely controlling the printer using the processor 102 will be described below. FIG. 28 is an explanatory diagram showing an example of a screen image presented on the screen of a monitor.

For example, an operator wants to enter a caption while observing an endoscopic image that is displayed on the screen of the monitor 103. The operator presses a Caption key that is a predetermined function key included in the keyboard 104. Consequently, a caption input window 126 that is a window dedicated to entering of a caption is, as shown in FIG. 28, opened with an endoscopic image 125 displayed on the screen of the monitor 103. A caption input standby state is thus set up.

An operator enters any caption at the keyboard 104, whereby the printer 106 prints the caption entered using the caption input window 126 at a predetermined position in the endoscopic image on print paper.

As mentioned above, when the caption window 126 is used to enter a caption, the keyboard 104 connected to the processor 102 should merely be manipulated. Compared with a case where a caption is entered at the main unit of the printer, manipulations are simplified.

However, the Caption key is not limited to a function key included in the keyboard 104. Alternatively, the Caption key may be any key that is unused to initiate any arithmetic operation, for example, a cursor or a Tab key, or a combination of keys, for example, a combination of a Ctrl key and a F2 key.

Incidentally, as far as the electronic endoscope system 100 is concerned, when patient data or a caption is entered at the keyboard 104, any of different input modes may be adopted. The input modes include an alphanumeric characters mode based on the ASCII, a katakana characters mode based on the romaji (that is Roman characters)-katakana conversion, and a katakana characters mode based on the kana-katakana conversion.

The input modes are changed using an Input Mode Change key that is a predetermined function key included in the keyboard 104.

Specifically, an input mode to which the keyboard 104 is set when the power supply is turned on is the ASCII-based input mode. When the Input Mode Change key is pressed in this state, the input mode is changed to the input mode based on the romaji-katakana conversion. When the Input Mode Change key is pressed again in this state, the input mode is changed to the input mode based on the kana-katakana conversion. When the Input Mode Change key is pressed again in this state, the input mode is returned to the ASCII-based input mode. In short, every time the Input Mode Change key is pressed, the input modes are changed cyclically in the order of the ASCII-based mode, the mode based on the romaji-katakana conversion, and the mode based on the kana-katakana conversion. This enables a user to change the input modes easily.

According to the present embodiment, the color of a cursor is varied depending on a current input mode. This helps a user recognize whether a current input mode is the ASCII-based input mode, the input mode based on the romaji-katakana conversion, or the input mode based on the kana-katakana conversion.

Specifically, when the ASCII-based input mode is designated, the cursor is displayed in white. When the input mode based on the romaji-katakana conversion is designated, the cursor is displayed in green. When the input mode based on the kana-katakana conversion is designated, the cursor is displayed in blue. Consequently, when a user changes the input modes, the user can immediately identify a current input mode at the sight of the color in which the cursor is displayed on the screen.

The Change key used to change the input modes is not limited to the function key included in the keyboard 104. Alternatively, the Change key may be any key that is unused to initiate any arithmetic operation, for example, a cursor or a Tab key, or a combination of keys, for example, a combination of a Ctrl key and a F3 key. Moreover, the colors of the cursor associated with the input modes are not limited to the foregoing ones. Any colors may be associated with the input modes.

By the way, the video signal processing unit 111 performs various kinds of signal processing on a video signal generated by the electronic endoscope 101. Photometry is included in the signal processing. For the photometry, the video signal processing unit 111 detects a luminance level which a video signal represents relative to each pixel location on a CCD, and distinguishes a bright part of all the pixel locations on the CCD from a dark part thereof. When data is acquired from almost all the pixel locations so that an endoscopic image represented by the data can be displayed on the screen of the monitor 103, photometry should be performed relative to all the pixel locations on the CCD. However, when data is acquired from only the center part of all the pixel locations so that an image represented by the data can be displayed on the monitor 103, if the perimeter of the CCD is involved in photometry, the photometry cannot be achieved properly.

Figure 29:
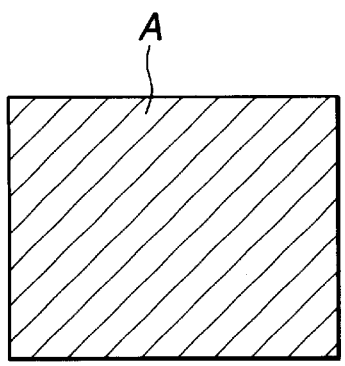
FIG. 29 is an explanatory diagram showing a whole-surface photometry mode.
Figure 30:
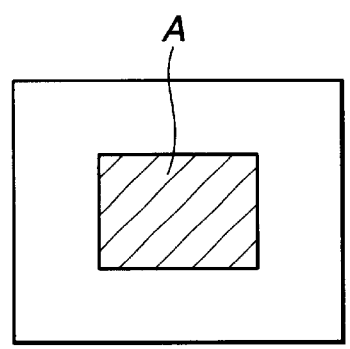
FIG. 30 is an explanatory diagram showing a center-emphasized photometry mode.
Figure 31:
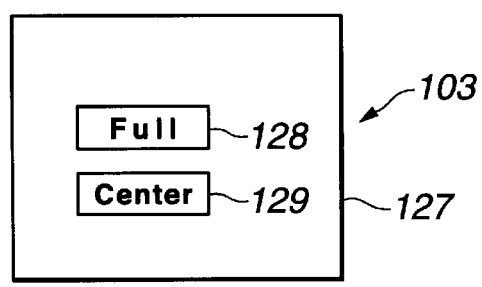
FIG. 31 shows an example of a screen image enabling switching of photometry modes.

In order to enable a user to define a photometric field A according to a situation using the processor 102, data must be acquired from almost all the pixel locations and an image represented by the data must be displayed on the screen of the monitor 103. In this case, whole-surface photometry is carried out as shown in FIG. 29. FIG. 29 is an explanatory diagram concerning whole-surface photometry. Referring to FIG. 29, a hatched area, that is, the whole surface matched with the whole screen is the photometric field A. When data is acquired from only the center part of all the pixel locations so that an endoscopic image represented by the data can be displayed on the screen of the monitor 103, center-emphasized photometry is carried out as shown in FIG. 30. FIG. 30 is an explanatory diagram concerning center-emphasized photometry. Referring to FIG. 30, a rectangular area matched with the center of the screen is the photometric field A. The photometry modes are changed using a system setup screen 127 shown in FIG. 31. FIG. 31 shows an example of a screen image that enables changing of the photometry modes.

The system setup screen 127 is displayed with a press of a System Setup key that is a predetermined function key (not shown) included in the keyboard 104. The system setup screen 127 has two fields associated with the two photometry modes; that is, a Full field 128 and a Center field 129. When the Full field 128 is clicked, the system setup screen is changed to the screen image, as shown in FIG. 29, associated with the whole-surface photometry. When the Center field 129 is clicked, the system setup screen is changed to the screen image, as shown in FIG. 30, associated with the center-emphasized photometry.

Once the system setup screen 127 is displayed, a user can easily select a photometry mode and observe a lesion with illumination light optimized.

The present invention is not limited to the aforesaid embodiments, but can be modified in various manners without a departure from the gist of the present invention.

What is claimed is:

1. An endoscope system having a lamp that emits illumination light with which an object is illuminated, and a power supply means that supplies power with which the lamp is lit, said endoscope system comprising:

a condition detecting means, provided to or near said lamp, for detecting a predetermined condition relevant to said lamp;

a notifying means for notifying a user of the state of said lamp according to a result of detection performed by said condition detecting means;

a selecting means for selecting a lamp from among a plurality of lamps included in said endoscope system; and a judging means for judging whether the lamp selected by said selecting means is located at a right position, wherein when said judging means judges that the lamp selected by said selecting means is not located at the right position, said notifying means notifies a user of the fact that the lamp is not located at the right position.

2. An endoscope system according to claim 1, further comprising a lamp holder that holds the plurality of lamps, wherein: said selecting means is a moving member that moves said lamp holder so that a selected lamp will be located on a path of illumination light and the other unselected lamp will be located at a standby position off the path of illumination light; and said judging means is a position sensing means that senses whether at least one of said plurality of lamps is located at a predetermined position.

3. An endoscope system according to claim 1, wherein said notifying means is a display control means that controls displaying on a predetermined display means so that predetermined visual information will be displayed on said display means according to the predetermined condition relevant to said lamp detected by said detecting means.

4. An endoscope system according to claim 1, wherein said notifying means is a sound control means that generates a predetermined sound according to the predetermined condition relevant to said lamp detected by said detecting means.

5. An endoscope system according to claim 1, wherein said notifying means is a display control means such that when said power detecting means detects that current or voltage supplied or applied to said lamp is equal to or smaller than a predetermined value, said display control means controls displaying on a display means predetermined visual information which indicates that current or voltage supplied or applied to said lamp is equal to or smaller than the predetermined value.

6. An endoscope system according to claim 1, wherein said notifying means is a generation control means such that when said power detecting means detects that current or voltage supplied or applied to said lamp is equal to or smaller than a predetermined value, said generation control means generates a predetermined sound which indicates that current or voltage supplied or applied to said lamp is equal to or smaller than the predetermined value.

* * * * *